US009809566B2

(12) United States Patent
Rawat et al.

(10) Patent No.: US 9,809,566 B2
(45) Date of Patent: Nov. 7, 2017

(54) ORGANOCATALYTIC PROCESS FOR ASYMMETRIC SYNTHESIS OF DECANOLIDES

(71) Applicant: Council of Scientific and Industrial Research, New Delhi (IN)

(72) Inventors: Varun Rawat, Pune (IN); Soumen Dey, Pune (IN); Anil Maruti Shelke, Pune (IN); Gurunath Mallappa Suryavanshi, Pune (IN); Arumugam Sudalai, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/167,337

(22) Filed: May 27, 2016

(65) Prior Publication Data

US 2016/0272609 A1 Sep. 22, 2016

Related U.S. Application Data

(62) Division of application No. 14/426,305, filed as application No. PCT/IN2013/000542 on Sep. 6, 2013, now Pat. No. 9,353,077.

(30) Foreign Application Priority Data

Sep. 6, 2012 (IN) .......................... 2765/DEL/2012

(51) Int. Cl.
  *C07D 313/04* (2006.01)
  *C07D 313/00* (2006.01)
(52) U.S. Cl.
  CPC ........ *C07D 313/00* (2013.01); *C07B 2200/07* (2013.01)
(58) Field of Classification Search
  CPC .................................................. C07D 313/00
  USPC ....................................................... 549/271
  See application file for complete search history.

(56) References Cited

U.S. PATENT DOCUMENTS

| 9,353,077 B2 | 5/2016 | Rawat et al. |
| 2015/0210665 A1 | 7/2015 | Rawat et al. |
| 2016/0272608 A1 | 9/2016 | Rawat et al. |

FOREIGN PATENT DOCUMENTS

WO WO-2014/037964 A2 3/2014

OTHER PUBLICATIONS

"U.S. Appl. No. 14/426,305, Examiner Interview Summary dated Dec. 31, 2015", 2 pgs.
"U.S. Appl. No. 14/426,305, Non Final Office Action dated Oct. 15, 2015", 6 pgs.
"U.S. Appl. No. 14/426,305, Notice of Allowance dated Feb. 2, 2016", 7 pgs.
"U.S. Appl. No. 14/426,305, Preliminary Amendment filed Feb. 5, 2015", 11 pgs.
"U.S. Appl. No. 14/426,305, Response filed Sep. 25, 2015 to Restriction Requirement dated Jul. 31, 2015", 10 pgs.
"U.S. Appl. No. 14/426,305, Response filed Dec. 10, 2015 to Non Final Office Action dated Oct. 15, 2015", 16 pgs.
"U.S. Appl. No. 14/426,305, Restriction Requirement dated Jul. 31, 2015", 8 pgs.
"International Application Serial No. PCT/IN2013/000542, International Preliminary Report on Patentability dated Mar. 10, 2015", 13 pgs.
"International Application Serial No. PCT/IN2013/000542, International Search Report dated Apr. 4, 2014", 5 pgs.
"International Application Serial No. PCT/IN2013/000542, Written Opinion dated Apr. 4, 2014", 12 pgs.
Das, Tapas, et al., "Chemoenzymatic total synthesis of stagonolide-E", Tetrahedron Letters, 53(2), (2012), 256-258.
Evidente, Antonio, et al., "Stagonolides G-I and Modiolide A, Nonenolides Produced by Stagonospora cirsii, a Potential Mycoherbicide for Cirsium arvense", Journal of Natural Products, 71(11), (2008), 1897-1901.
Kamal, Ahmed, et al., "Novel Synthesis of Stagonolide-F, Putaminoxin and Aspinolide-A", (Abstract), Letters in Organic Chemistry, 8(2), (2011), 143-149.
Krishna, Palakodety R., "Stereoselective Total Synthesis of (−)-(6R,11R,14R)-Colletallol via RCM Protocol", Synlett 2009(18), (2009), 2924-2926.
Mahapatra, T., et al., "Asymmetric synthesis of stagonolide-D and stagonolide-G", Bull. Chem. Soc. Jpn,, 84(5), (2011), 511-519.
Perepogu, Arun Kumar, "Concise synthesis of stagonolide-F by ring closing metathesis approach and its biological evaluation", Bioorganic Chemistry, 37(2), (2009), 46-51.
Prabhakar, Peddikotla, et al., "Total synthesis of the phytotoxic stagonolides A and B", Tetrahedron: Asymmetry 21, (2010), 216-221.
Prebhakar, Peddikotla, et al., "Total synthesis of the phytotoxic stagonolides A and B", Tetrahedron: Asymmetry 21(2), (Feb. 22, 2010), 216-221.
Racherla, Uday S, et al., "Chiral Synthesis via Organoboranes. 27. Remarkably Rapid and Exceptionally Enantioselective (Approaching 100% ee) Allylboration of Representative Aldehydes at -100. degree. under New, Salt-Free Conditions", The Journal of Organic Chemistry, 56(1), (1991), 401-404.
Shelke, Anil M, et al., "Asymmetric synthesis of (+)-stagonolide C and (−)-aspinolide A via organocatalysis", Tetrahedron: Asymmetry 23(22-23), (2012), 1534-1541.
Srihari, P., et al., "First stereoselective total synthesis of stagonolide G", Tetrahedron Letters. 51(21), (2010), 2903-2905.
Wu, Jian-Zhong, et al., "Synthesis of stagonolide C from Mulzer epoxide", Tetrahedron Letters, 53(9), (2012), 1153-1155.

(Continued)

*Primary Examiner* — Nizal Chandrakumar
(74) *Attorney, Agent, or Firm* — Schwegman Lundberg & Woessner, P.A.

(57) ABSTRACT

The present invention discloses organocatalytic process for asymmetric synthesis of highly enantioselective decanolide compounds in high yield with >99% ee. Further, the present invention disclose cost effective, improved organocatalytic process for asymmetric synthesis of highly enantioselective decanolides compounds from non-chiral, cheap, easily available raw materials.

1 Claim, No Drawings

(56) References Cited

OTHER PUBLICATIONS

Yadav, Jhillu S., et al., "Stereoselective Total Synthesis of Stagonolide C", Helvetica Chimica Acta, 95(2), (2012), 227-334.
U.S. Appl. No. 15/167,298, filed May 27, 2016, Organocatalytic Process for Asymmetric Synthesis of Decanolides.
"U.S. Appl. No. 15/167,298, Non-Final Office Action dated Jan. 19, 2017", 5 pgs.
"U.S. Appl. No. 15/167,298, Response filed Apr. 4, 2017 to Non-Final Office Action dated Jan. 19, 2017", 6 pgs.

ORGANOCATALYTIC PROCESS FOR ASYMMETRIC SYNTHESIS OF DECANOLIDES

CROSS-REFERENCE TO RELATED APPLICATIONS

This application is a divisional and claims the benefit of priority of U.S. application Ser. No. 14/426,305, filed 5 Mar. 2015, which is a U.S. National Stage Filing under 35 U.S.C. §371 from International Application No. PCT/IN2013/000542, filed on 6 Sep. 2013, and published as WO2014/037964 on 13 Mar. 2014, which application claims the benefit of priority to Indian Application No. 2765/DEL/2012, filed on 6 Sep. 2012; which applications and publication are incorporated herein by reference and made a part hereof in their entirety, and the benefit of priority of each of which is claimed herein.

TECHNICAL FIELD

The present invention provides organocatalytic process for asymmetric synthesis of highly enantioselective decanolide compounds in high yield with >99% ee.

Further present invention provides cost effective, improved organocatalytic process for asymmetric synthesis of highly enantioselective decanolides compounds from non-chiral, cheap, easily available raw materials.

BACKGROUND AND PRIOR ART

Decanolides, isolated from various fungal metabolites have attracted considerable attention due to the interesting biological properties and scare availability of macrolides. Aspinolide A, its diastereomer Stagonoide F, Stagonolide C, Stagonolide E and several other decanolides have been isolated from cultures of various fungii. Few syntheses of these important Macrolides are known most of which involves the use of kinetic resolution for generating chirality or based on chiral pool approach involving large number of steps.

T. Mahapatra et al. in *Bull. Chem. Soc. Jpn.*, 2011, 84 (5), 511-519 describes efficient asymmetric synthesis of naturally occurring small ring macrolide, stagonolide-D and stagonolide-G from (S)-ethyl lactate as a chiral pool. Further a convergent and efficient total synthesis of stagonolide C exploits the high configuration control in the Prins cyclization along with alkene rearrangement and ring-closing metathesis as key steps is reported. in *Helvetica Chimica Acta*. 95 (2) 227-324 February 2012 by Jhillu S. Yadav et al. The nonenolides such as Stagonolides G to Stagonolides I and Modiolide A are disclosed in *J. Nat. Prod.*, 2008, 71 (11), 1897-1901. The stereoselective total synthesis of Stagonolide G is disclosed in *Tetrahedron Letters*, 51 (21) 2010, 2903-2905.

The stereoselective total synthesis of the nonenolide, (+)-stagonolide B involves epoxide homologation, hydrolytic kinetic resolution and ring-closing metathesis is described in Synthesis 2010(6): 1039-1045.

*Tetrahedron Letters* 53, (2) January 2012, 256-258 discloses chemoenzymatic asymmetric total synthesis of small ring macrolide stagonolide-E comprises ruthenium(II), enzyme combo dynamic kinetic resolution reaction, whereas *Synlett* 2009 (18) 2924-2926 describes stereoselective total synthesis of (−)-(6R,11R,14R)-Colletallol comprises Jacobsen's hydrolytic kinetic resolution (HKR) and ring-closing metathesis protocol.

Further the synthesis of 9-membered macrolide, stagonolide-F (3), wherein Jacobsen's hydrolytic kinetic resolution (HKR) and Sharpless epoxidation is used for the creation of two stereogenic centers is reported in *Bioorganic Chemistry* 37 (2), 2009, 46-51.

*Tetrahedron Letters* 53, (9), February 2012, 1153-1155 discloses total synthesis of stagonolide C using chiral pool strategy. Novel synthesis of putaminoxin, stagonolide-F and aspinolide-A have been achieved by utilizing (S) and (R)-malic acid is known from *Letters in Organic Chemistry*, 8, (2), February 2011, 143-149 (7).

In view of foregoing most of the process in the prior art involves chiral pool strategy, use of expensive and toxic metal catalyst, also gives poor yield and entioselectivity of desired decanolides or nonenolides. Further, the lengthy steps in the prior art impact the overall yield of the decanolides.

The present inventors therefore felt a need to develop enantioselective synthesis of biologically active natural product based on asymmetric organocatalysis by a simple, concise and flexible route with reduced number of process steps using non chiral, cheaper, easily available starting material.

OBJECT OF INVENTION

The main objective of the present invention is to provide cost-effective and improved organocatalytic process for asymmetric synthesis of highly enantioselective decanolide compounds.

SUMMARY OF THE INVENTION

Accordingly, the present invention provides an organo catalytic process for preparation of decanolides of Formula Ia with high enantioselectivity,

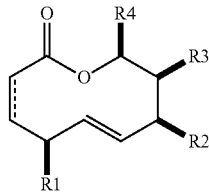

Formula Ia wherein, R1, R2, R3 and R4 are independently selected from the group consisting of H, OH, substituted or un substituted ($C_1$-$C_5$) alkyl; or R2 and R3 may together form an epoxy ring; (-----) represents either single or double bond, (———) represents cis or trans position of the substituents R1 to R4 i.e. (either ━━ or ⋯⋯);
wherein the said process comprising the steps of;
i. enantioselective allylboration of aldehyde (1) in presence of allyldiisopinocamphenylborane at temperature in the range of −120° C. to −80° C. for 1-2 hrs in non-polar organic solvents selected from diethyl ether, pentane, cyclopentane, benzene, toluene, 1,4-dioxane, chloroform or mixtures thereof followed by treatment with NaOH and aqueous $H_2O_2$ to obtain chiral allylic alcohol (3);
ii. protecting chiral allylic alcohol (3) as obtained in step (i) with TBS by treating with TBSCl, imidazole, in a polar aprotic solvents selected from DMF, DCM, THF, ethyl acetate, acetone, DMSO to obtain compound (4)

followed by Wittig reaction by reacting Wittig reagent. Ph₃P=CHCO₂Et in a polar aprotic solvents preferably THF to obtain corresponding α-β unsaturated ester (5);

iii. reducing α-β unsaturated ester (5) as obtained in step (ii) in presence of DIBAL-H in toluene at temperature range −80° C. to −50° C. to obtain α,β-unsaturated aldehyde (6) followed by organocatalytic Jørgensen epoxidation of α,β-unsaturated aldehyde (6) in presence of a chiral bisaryl-silyl-protected pyrrolidine preferably bis(3,5-bis(trifluoromethyl)phenyl)trimethyl silyloxy) methyl]pyrrolidine in the range of 5% to 20% and hydrogen peroxide and polar aprotic solvents selected from DMF, DCM, THF, ethyl acetate, acetone, DMSO at ambient temperature ranging between 25-35° C. for a period followed by reduction in presence of NaBH₄ in lower alcohol selected from methanol, ethanol, n-propanol, iso-propanol, n-butanol at temperature range −5° C. to 5° C. to obtain enantiomerically enriched epoxy alcohol compound (7);

iv. stirring epoxy alcohol (7) in presence of triphenylphosphine, iodine and imidazole reagent in an organic solvent selected from the group consisting of diethyl ether, DMF, DCM, THF, ethyl acetate, acetone, acetonitrile, methanol, ethanol or mixtures thereof followed by treatment with Zn and NaI in methanol to obtain allylic alcohol (9) and further protecting allylic alcohol (9) with MOM in presence of MOMCl, DIPEA in DCM solvent to obtain compound (10) followed by deprotection of TBS to afford MOM protected allylic alcohol (11);

v. esterification of MOM protected allylic alcohol (11) with MOM protected carboxylic acid compound (12) in presence of EDCl and DMAP in a polar solvent DCM to obtain ester compound (13); and ring-closing metathesis of ester compound (13) with Grubbs second generation carbene complex, followed by deprotection of MOM to obtain Formula Ia.

In one embodiment of the present invention compound of Formula Ia is selected from the group of Stagonolide C or Modiolide A.

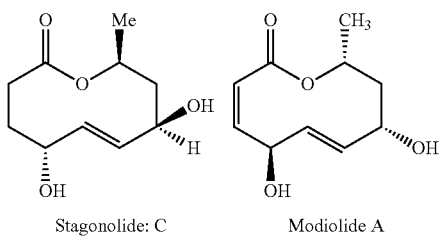

Stagonolide: C         Modiolide A

In an embodiment of the present invention an organo catalytic process for preparation of decanolides of Formula Ib with high enantioselectivity

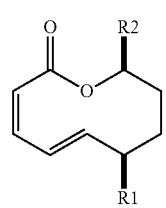

Formula Ib wherein, R1 and R2 are independently selected from —OH or —H, substituted or un-substituted ($C_1$-$C_5$) alkyl; (———) bond represents either cis or trans position of the R1 and R2 i.e. (either ——— or ~~~~).

with the proviso, when R1 is —OH either in cis or trans position; R2 is methyl group either in cis or trans position;

wherein, the said process comprising the steps of;

i. protecting one of the terminal hydroxyl group of diol (21) with benzyl group by using benzyl bromide in dry THF to obtain corresponding mono-benzyl ether (22), followed by TEMPO catalyzed oxidation in presence of iodobenzene diacetate in organic solvent selected from DCM, DMF to obtain benzyl protected aldehyde (23);

ii. proline-catalyzed direct asymmetric α-aminoxylation of benzyl protected aldehyde (23) using nitrosobenzene in acetonitrile as an oxygen source, followed by treatment with NaBH₄ in methanol further treating with copper (II) acetate in methanol for 24 hrs (10-20 mins) at temperature ranging between to obtain chiral diol (24), which is further treated with dibutyl tin oxide and tosyl chloride, triethylamine in DCM furnishes the mono tosylated compound, which is further treated with potassium carbonate in dry methanol at 0-25° C. for 20-40 mins to obtain epoxy compound (25);

iii. reducing epoxy compound (25) in presence of LAH to chiral secondary alcohol (26), subsequently protecting with TBS by using TBS-Cl, imidazole in DCM followed by deprotection of benzyl in presence of palladium catalyzed reduction in ethyl acetate gives TBS protected alcohol (28); followed by TEMPO catalyzed oxidization in presence of iodobenzene diacetate in organic solvent preferably DCM to obtain aldehyde compound (29);

iv. catalytic Horner-Wadsworth-Emmons olefinating and concomitant copper catalyzed oxidizing of compound (29) to yield hydroxyl ester (30), further protecting with MOM in presence of MOMCl and DIPEA in DCM to corresponding protected ester (31);

v. reducing the protected ester (31) using DIBAL-H in dry DCM at temperature range from −70° C. to −85° C. to obtain aldehyde (32), followed by Wittig reaction in dry THF at temperature range from −70° C. to −85° C. to obtain corresponding ester (33); further deprotecting of TBS in presence of TBAF in THF to secondary alcohol (34), followed by alkali hydrolysis of the ester with LiOH in methanol and water to carboxylic acid (35); and vi. yamaguchi macrolactonizing of (35) in presence of 2,4,6 trichloro benzoyl chloride and triethylamine in THF and DMAP in toluene to obtain the MOM protected decanolide (36) subsequently deprotecting of MOM to obtain decanolides of Formula Ib.

In another embodiment of the present invention the decanolides of Formula Ib is

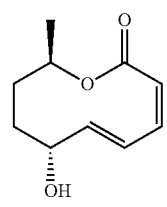

Stagonolide E

In another embodiment of the present invention an organo catalytic process for the preparation of decanolides of Formula Ic with high enantioselectivity

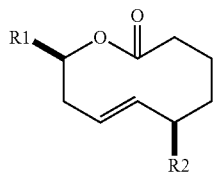

Formula Ic wherein R1 and R2 is independently selected from the group consisting of H, OH, substituted or unsubstituted ($C_1$-$C_5$) alkyl; (———) represents cis or trans position of R1 and R2 i.e. (either ——— or ·····)

with the proviso, when, R1 is methyl either in cis or trans position; R2 is —OH on the same position with regard to R1 wherein the said process comprising the steps of;
  i. enantioselective allylboration of aldehyde (1) in presence of allyldiisopinocamphenylborane at temperature in the range of −120° C. to −80° C. for 1-2 hrs in non-polar organic solvents selected from diethyl ether, pentane, cyclopentane, benzene, toluene, 1,4-dioxane, chloroform or mixtures thereof followed by treatment with NaOH and aqueous $H_2O_2$ to obtain chiral allylic alcohol (3);
  ii. esterification of allylic alcohol (3) with TBS protected carboxylic acid (15) in presence of EDCl HCl, DMAP in DCM at temperature range 0° to 30° C. for 5 to 8 hrs with subsequent deprotection of TBS in presence of TBAF in THF for 6-8 hrs yields allylic alcohol (17); and
  iii. ring closing metathesis reaction of compound (17) in presence of Grubbs II catalyst (5 to 15%) in dry DCM for 18-24 hrs to obtain decanolides of Formula Ic In yet another embodiment of the present invention decanolides of Formula Ic is Aspinolide A.

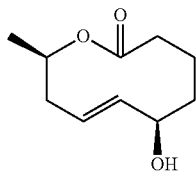

Aspinolide: A

In still another embodiment of the present invention MOM protected carboxylic acid used in step (v) and (ii) respectively is obtained by said process comprising;
  i. protecting one of the hydroxyl group of 1,2 diol with TBS in presence of TBS-Cl, imidazole in polar organic solvent selected from DCM, DMF, THF, ethyl acetate, acetone, DMSO at temperature range 0° C. to 30° C. for 5-8 hrs to give mono TBS substituted alcohol further subjecting the alcohol (2a) to TEMPO catalyzed oxidation in presence of iodobenzene diacetate in polar organic solvent such as DCM at temperature range 20° C. to 30° C. followed by Wittig olefination with $Ph_3P$=CHCOOEt in THF at ambient temperature ranging between 25-35° C. for 10-15 hrs results in olefin ester;
  ii. reducing olefin ester (3a) using DIBAL-H in toluene at temperature −80° C. to −60° C. for 0.5 to 2 hrs to obtain protected aldehyde;
  iii. subjecting protected aldehyde of step (ii) to epoxidation in presence of a chiral bisaryl-silyl-protected pyrrolidine in the range of 5% to 20% at ambient temperature to enantiomerically enriched epoxy alcohol;
  iv. converting epoxy alcohol of step (iii) into epoxy iodide in presence of iodine-triphenylphosphine-imidazole reagent in an organic solvent selected from diethyl ether, DMF, DCM, THF, ethyl acetate, acetone, acetonitrile, methanol, ethanol or mixtures thereof under reflux for 2-4 hrs with Zn and NaI to obtain allylic alcohol;
  v. protecting chiral hydroxy group of alcohol of step (iv) with MOM in presence of -MOMCl, DIPEA in DCM as solvent to obtain TBS ether followed by deprotection with CSA in methanol at ambient temperature in 5-10 mins to compound;
  vi. oxidizing compound of step (v) using iodobenzene diacetate and TEMPO, in presence of water miscible polar organic solvent preferably acetonitrile to obtain chiral protected carboxylic acid;
  vii. or optionally chiral protected carboxylic acid is obtained by protecting one of the hydroxyl group of 1,2 diol with TBS in presence of TBS-Cl, imidazole in polar organic solvent selected from DCM, DMF, THF, ethyl acetate, acetone, DMSO at temperature range of 0° C. to 30° C. for 5-8 hrs to give mono TBS substituted alcohol and subjecting to TEMPO catalyzed oxidation in presence of iodobenzene diacetate in polar organic solvent selected from DCM at room temperature for 1-2 hrs to obtain protected aldehyde;
  viii. α-hydroxylation of aldehyde of step (vii) in presence of proline using nitrosobenzene in acetonitrile at temperature in the range of −25° C. to −10° C. for 20-30 hrs followed by in-situ reduction of hydroxyl aldehyde and treating with copper(II)acetate in methanol to obtain corresponding chiral diol;
  ix. selective tosylation of chiral diol of step (viii) using tosyl chloride, triethylamine, and catalytic amount of dibutyltin oxide ($Bu_2SnO$) in DMAP furnishes the mono tosylated compound, further treating with potassium carbonate in dry methanol at 0° C.-25° C. for 20-40 mins to obtain the epoxide followed by ring closure in presence of base to epoxide and converting to allylic alcohol by refluxing in the presence of 12, Imidazole, $CH_3CN$, diethyl ether, NaI, Zn and MeOH;
  x. protecting allylic alcohol of step (ix) with MOM by using MOMCl, DIPEA in DCM as solvent and deprotecting alcohol with CSA in methanol at ambient temperature ranging between 25-35° C. in 5-10 mins and subjecting alcohol to TEMPO catalyzed oxidation using iodobenzene diacetate in presence of water miscible polar organic solvent such as methanol, acetonitrile preferably mixture of ACN:water in (4:1) ratio at room temperature 25-35° C. for 3 to 4 hrs to obtain chiral protected carboxylic acid.

In still another embodiment of the present invention enantioselectivity of compound of formula Ia, formula Ib and formula Ic is in the range of 98-99%.

In still another embodiment of the present invention yield of compound of formula Ia, formula Ib and formula Ic is in the range of 20-35%.

In still another embodiment of the present invention yield of MOM protected carboxylic acid is in the range of 50-98%.

In still another embodiment of the present invention chirality is introduced in the said compounds in process steps of proline catalyzed asymmetric α-aminoxylation and/or epoxidation of aldehydes.

DETAILED DESCRIPTION

The invention will now be described in detail in connection with certain preferred and optional embodiments, so that various aspects thereof may be more fully understood and appreciated.

Abbreviations

Bu₂SnO: Dibutyltin oxide
CSA: Camphorsulfonic acid
DMAP: 4-Dimethylaminopyridine
DMSO: Dimethyl sulfoxide
DIBAL-H: Diisobutylaluminium hydride
DIPEA: N,N-Diisopropylethylamine
EDCl: N-(3-dimethylaminopropyl)-N'-ethylcarbodiimide hydrochloride
MOM: Methoxy methyl ether
NaBH₄: Sodium borohydride
Et₃N: Triethylamine
Ph₃PCH₃I: methyiodideltriphenylphosphonium (Wittig reagent)
PhNO: Nirosophenyl
Ph₃P=CHCO₂Et: ethyl triphenyiphosphoranylidene acetate
[Ru(BINAP)Cl₂]: Ru-diphosphine complexes
BINAP: 2,2'-bis(diphenylphosphino)-1,1'-binaphthyl
TBAF: Tetra-n-butylammonium fluoride
TBS: tert-butyldimethylsilyl
TEMPO: (2,2,6,6-Tetramethylpiperidin-1-yl)oxyl, or (2,2,6,6-tetramethylpiperidin-1-yl)oxidanyl
THF: Tetrahydrofuran The present invention in pursuit of developing a concise method for synthesis of biologically active natural compounds of the group decanolides with high enantioselectivity i.e. >99% provides organo catalyzed asymmetric synthesis of decanolides. The said process is simple, flexible with reduced number of steps. The inventive feature in the instant process lies in the use of process steps such as proline catalyzed asymmetric α-aminoxylation and Jorgensen's epoxidation of aldehydes for introduction of chirality to obtain chiral intermediates that can lead to formation of said chiral decanolides thus making the process highly selective with specificity towards enatio selectivity usually >99% and with increased yields. Further the use of orgnocatalyst makes the process environmentally feasible and cost effective.

In preferred embodiment, the present invention provides cost-effective, non-toxic, organocatalytic process for the asymmetric synthesis of highly enantioselective decanolides compounds with more than 99% ee In preferred embodiment, the present invention provides organocatalytic process for the asymmetric synthesis of decanolide compounds having Formula Ia;

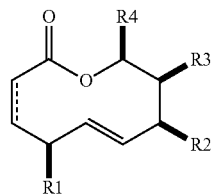

Formula Ia wherein, R1, R2, R3 and R4 is independently selected from the group consisting of H, OH, substituted or un substituted ($C_1$-$C_5$) alkyl; or R2 and R3 may together form an epoxy ring; (-----) represents either single or double bond, (———) represents cis or trans position of the substituents R1 to R4 i.e. (either ▬ or ⁙⁙⁙);

with the proviso, when R1, R2 and R3 is —OH either in cis or trans position; R4 represents n-propyl either in cis or trans position; the compound is Stagonolide-B;

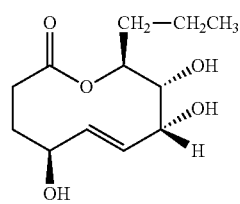

Stagonolide: B with the proviso, when R1 and R2 is —OH either in cis or trans position; R4 represents methyl either in cis or trans position; the compound is Stagonolides-C; and

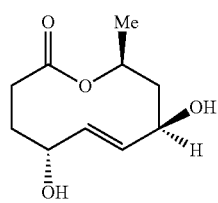

Stagonolide: C with the proviso, when R1 is —OH either in cis or trans position; R2 and R3 is together form epoxy ring either in cis or trans position; R4 represents methyl either in cis or trans position; the compound is Stagonolides-D; and

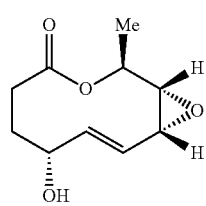

Stagonolide: D with the proviso, when R1 and R2 is —OH either in cis or trans position; R4 represents methyl group either in cis or trans position; the compound is Modiolide-A;

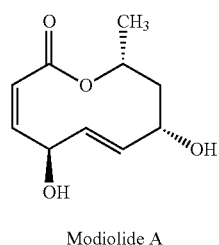

Modiolide A

In a preferred embodiment, the present invention provides an organocatalytic process for the preparation of compound of Formula Ia; preferably Stagonolide C or Modiolide A (as shown in Scheme 1) comprising;

a) enantioselective allylboration of aldehyde (1) to obtain allylic alcohol (3), protected with TBS to obtain compound (4), followed by Wittig reaction to obtain corresponding ester (5);

b) reduction of ester (5) in presence of DIBAL-H to obtain aldehyde (6), followed by epoxidation to yield enantiomerically enriched epoxy alcohol (7);

c) conversion of compound (7) to allylic alcohol (9) in presence of triphenylphosphine, iodine and imidazole reagent followed by treatment with Zn and NaI in alcohol, and further protection with MOM to obtain compound (10) followed by deprotection of TBS to afford alcohol (11);

d) esterification of MOM protected allylic alcohol (11) with carboxylic acid compound (12) to obtain ester compound (13); and e) ring-closing metathesis of ester compound (13), followed by deprotection of MOM to yield the desired dacanolides; Stagonolide C or Modiolide A.

Scheme 1:

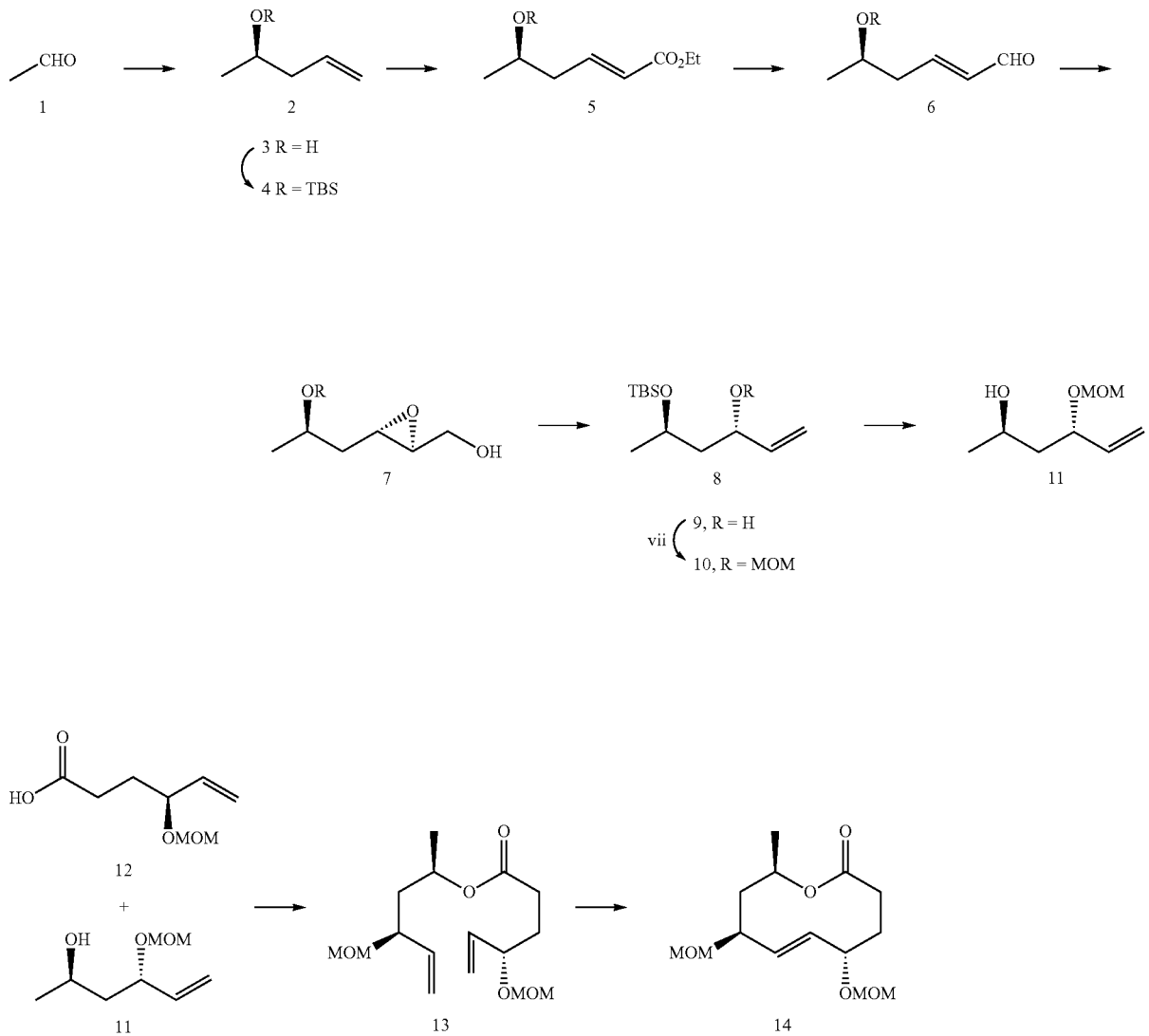

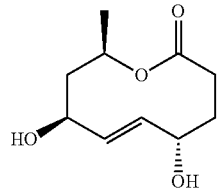

Stagonolide C

Reagents and conditions:
(i) TBSCl, imid, CH$_2$Cl$_2$, 0-25° C., 6 h, 76%
(ii) ethyl acrylate, Grubbs-II (10 mol%), dry CH$_2$Cl$_2$, reflux, 12 h, 65%,
(iii) DIBAL-H, toluene, –78° C., 1 h, 73%;
(iv) H$_2$O$_2$, CH$_2$Cl$_2$, (10 mol%) (R)-a,a–Bis[3,5-bis(trifluoromethyl)phenyl]-2-pyrrolidinemethanol, tri-methylsilyl ether, 25° C., 4 h then NaBH$_4$, MeOH, 0° C., 1 h, 53%;
(v) (a) I$_2$, PPh$_3$, imid., Et$_2$O/CH$_3$CN (3:1), 0-25° C., 2 h; (b) Zn, NaI, MeOH, reflux, 3 h, 90% (for two steps); (vi) MOMCl, DIPEA, dry CH$_2$Cl$_2$, 16 h, 90%; (vii) TBAF, THF, 2 h, 82%.

In accordance with scheme 1, the aldehyde compound (1) undergoes enantioselective allylboration in presence of allyldiisopinocamphenylborane at temperature in the range of −120° C. to −80° C. for 1-2 hrs in non-polar organic solvents such as, diethyl ether, pentane, cyclopentane, benzene, toluene, 1,4-dioxane, chloroform or mixtures thereof; preferably mixture of diethyl ether-pentane, followed by treatment with NaOH and aqueous H$_2$O$_2$ to obtain chiral allylic alcohol (3) in 75% yield with 99% ee. Further the sec alcohol compound (3) is protected with TBS group by treating with TBSCl, imidazole, in suitable polar aprotic solvents such as DMF, DCM, THF, ethyl acetate, acetone, DMSO etc. gives protected compound (4) which is further treated with Wittig reagent i.e. Ph$_3$P=CHCO$_2$Et in suitable polar aprotic solvents to get α-β unsaturated ester (5). The reduction of ester (5) gives α,β-unsaturated aldehyde (6) in presence of DIBAL-H in toluene at temperature range −80° C. to −50° C. Further the asymmetric organocatalytic Jørgensen epoxidation of α,β-unsaturated aldehydes with hydrogen peroxide in polar aprotic solvents such as DMF, DCM, THF, ethyl acetate, acetone, DMSO etc. affords enantiomerically enriched epoxy alcohol (7), wherein the Jorgensen epoxidation takes place in presence of a chiral bisaryl-silyl-protected pyrrolidine; preferably bis(3,5-bis(trifluoromethyl)phenyl)trimethyl silyloxy) methyl]pyrrolidine having molar concentration in the range of 5% to 20% at ambient temperature followed by reduction in presence of NaBH$_4$ in lower alcohol such as methanol, ethanol, n-propanol, iso-propanol, n-butanol at temperature range −5° C. to 5° C. The obtained epoxy alcohol (7) is thus converted into epoxy iodide in presence of iodine-triphenylphosphine-imidazole reagent in suitable organic solvent such as diethyl ether, DMF, DCM, THF, ethyl acetate, acetone, acetonitrile, methanol, ethanol or mixtures thereof; preferably mixture of diethyl ether and acetonitrile in (3:1) ratio, which is further refluxed with Zn and NaI in MeOH affords the secondary allylic alcohol (9), subsequent protection with MOM in presence of MOMCl, DIPEA in DCM solvent followed by deprotection of TBS gives the MOM protected allylic alcohol (11).

Further the alcohol (11) is esterified in presence of EDCl and DMAP in suitable polar solvent such as DCM with MOM protected carboxylic acid (12) to get ester (13) in 86% yield, wherein carboxylic acid (12) is synthesized by different methods. The obtained ester (13) is then subjected to ring closing metathesis reaction with Grubbs second generation carbene complex to obtain MOM protected decanolides (14) which is further deprotected gives desired decanolides, such as Stagonolide C or Modiolide A (from Stagonolide C Modiolide A can be synthesized in two steps by literature known procedure).

In another embodiment, the MOM protected carboxylic acid (12) can be synthesized by two methods. The first method for the preparation of MOM protected carboxylic acid (12) is illustrated in scheme 2.

Scheme 2:

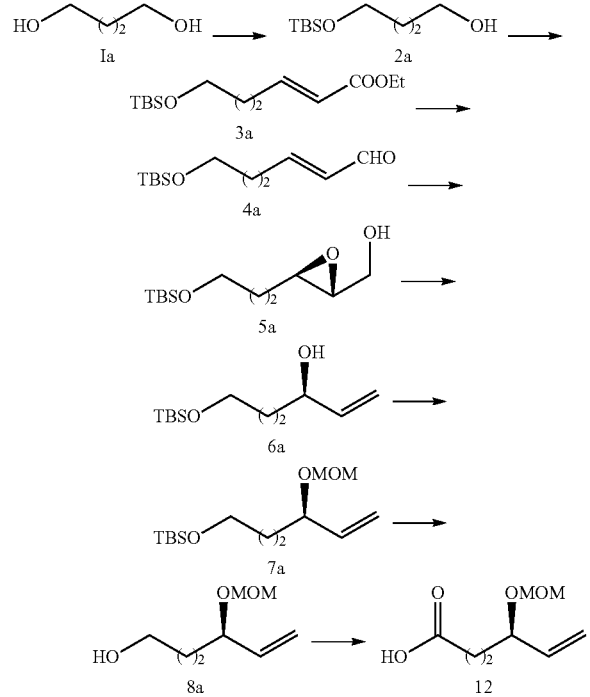

Reagents and conditions:
(i) (a) PhNO (1 equiv.), D-proline (20 mol %), CH$_3$CN, -20 °C., 24 h then NaBH$_4$, MeOH, 0° C., 1 h; (b) 10% Pd/C, H$_2$, MeOH, 24 h, 77% (over two steps);
(ii) (a) TsCl, Et$_3$N, Bu$_2$SnO, DMAP; (b) K$_2$CO$_3$, MeOH, 30 min., 92%;
(iii) S$^+$(CH$_3$)$_3$I$^-$, NaH, DMSO, 25° C. 2 h, 87%;
(iv) MOMCl, DIPEA, dry CH$_2$Cl$_2$, 16 h, 90%;
(v) TBAF, THF, 2 h, 88%;
(vi) TEMPO, PhI(OAc)$_2$, CH$_3$CN: H$_2$O (4:1), 25° C., 4 h, 86%.

In accordance with scheme 2, the 1,4 diol (1a) is protected with TBS in presence of TBS-Cl, imidazole in polar organic solvent such as DCM, DMF, THF, ethyl acetate, acetone, DMSO at temperature range 0° C. to 30° C. for 5-8 hrs to give mono TBS substituted alcohol (2a) in 66% yield.

Further the alcohol (2a) is subjected to TEMPO catalyzed oxidation in presence of iodobenzene diacetate in polar organic solvent such as DCM at temperature range 20° C. to 30° C. followed by Wittig olefination with Ph$_3$P=CHCOOEt in THF at ambient temperature for 10-15 hrs results in olefin ester (3a) in 93% yield. Further the reduction of olefin ester (3a) using DIBAL-H in toluene at temperature -80° C. to -60° C. for 0.5 to 2 hrs gives 73% yield of olefin aldehyde (4a). The asymmetric organocatalytic Jorgensen epoxidation of (4a) affords enantiomerically enriched epoxy alcohol (5a) in 53% yield, followed by reduction in presence of NaBH$_4$ in lower alcohol such as methanol, ethanol, n-propanol, iso-propanol, n-butanol at temperature range -5° C. to 5° C. for 0.5 to 2 hrs. The obtained epoxy alcohol (5a) is thus converted into epoxy iodide in presence of iodine-triphenylphosphine-imidazole reagent in suitable organic solvent such as diethyl ether, DMF, DCM, THF, ethyl acetate, acetone, acetonitrile, methanol, ethanol or mixtures thereof; preferably mixture of diethyl ether and acetonitrile in (3:1) ratio, which under reflux for 2-4 hrs with Zn and NaI in MeOH affords the secondary allylic alcohol (6a) in 90% yield, subsequently the hydroxyl group of (6a) is protected with MOM in presence of -MOMCl, DIPEA, r.t in DCM as solvent to afford primary TBS ether (7a), which is selectively cleaved with CSA in methanol at ambient temperature in 5-10 mins to afford alcohol (8a) in 63% yield. Further the oxidation of alcohols (8a) using iodobenzene diacetate and TEMPO, in presence of water miscible polar organic solvent such as methanol, acetonitrile (ACN); preferably mixture of ACN: water in (4:1) ratio at room temperature for 3 to 4 hrs to obtain MOM protected carboxylic acid (12) in 80% yield, wherein addition of a trace of water is found to be crucial for complete conversion of alcohol into corresponding acid (12).

Alternately, the second method for the preparation of MOM protected carboxylic acid (12) is illustrated in scheme 3.

Scheme 3:

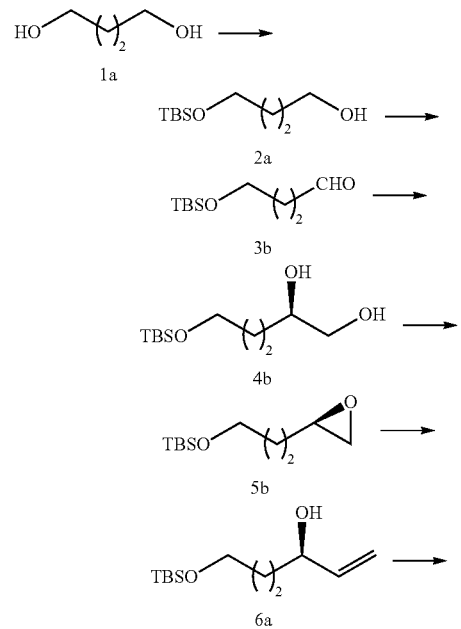

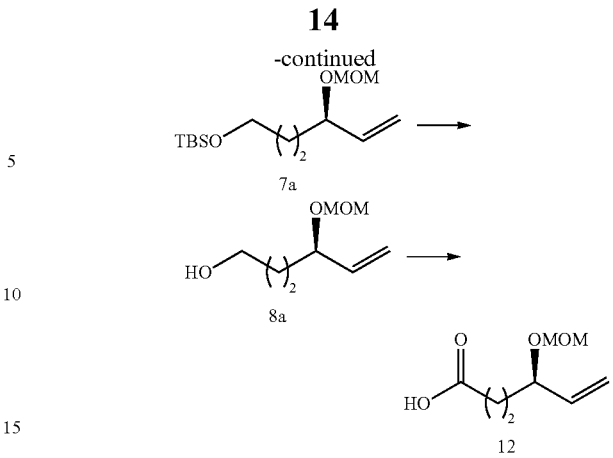

Reagents and conditions:
(i) TBSCl, Imid, CH$_2$Cl$_2$, 0-25° C., 76%;
(ii) Tempo, PhI(OAc)$_2$, 25° C., 85%;
(iii) (a) PhNO (1 equiv.), D-proline (20 mol %), CH$_3$CN, -20° C., 24 h then NaBH$_4$, MeOH, 0° C., 1 h; (b)Cu(OAc)$_2$, MeOH, 24 h, 67% (over two steps);
(iv) (a) TsCl, Et$_3$N, Bu$_2$SnO, DMAP; (b) K$_2$CO$_3$, MeOH, 30 min., 92%;
(v) S$^+$CH$_3$)$_3$I$^-$, NaH, DMSO, 25° C., 2 h, 87%;
(vi) MOMCl, DIPEA, dry CH$_2$Cl$_2$, 16 h, 90%;
(vii) CSA, MeOH, 2 h, 636;
(viii) TEMPO, PhI(OAc)$_2$, CH$_3$CN: H$_2$O (4:1), 25° C., 4 h, 86%.

In accordance with scheme 3, the 1,4 diol (1a) is protected with TBS in presence of TBS-Cl, imidazole in polar organic solvent such as DCM, DMF, THF, ethyl acetate, acetone, DMSO at temperature range of 0° C. to 30° C. for 5-8 hrs to give mono TBS substituted alcohol (2a) in 76% yield. Further the alcohol (2a) is subjected to TEMPO catalyzed oxidation in presence of iodobenzene diacetate in polar organic solvent such as DCM at room temperature for 1-2 hrs to obtain aldehyde (3b) in 85% yield, further (3b) is exposed to proline-catalyzed α-hydroxylation protocol using nitrosobenzene in acetonitrile at temperature range of -25° C. to -10° C. for 20-30 hrs, followed by the in situ reduction of the resultant hydroxy aldehyde using sodium borohydride (NaBH$_4$) in methanol, further obtained compound is treated with copper(II)acetate in methanol which provides the corresponding chiral diol (4b) in 67% yield. The selective tosylation of the diol (4b) using tosyl chloride, triethylamine, and catalytic amount of dibutyltin oxide (Bu$_2$SnO) in DMAP furnishes the mono tosylated compound, which is further treated with potassium carbonate in dry methanol at 0° C. for 20-40 mins to obtain the epoxide (5b) in 92% yield. The epoxide is then converted into allylic alcohol (6a) by refluxing in the presence of I2, Imidazole, CH$_3$CN, diethyl ether, NaI, Zn and MeOH. The hydroxyl group of (6a) is protected with MOM by using MOMCl, DIPEA, rt in DCM as solvent. Further the primary TBS ether (7a) is selectively cleaved with CSA in methanol at ambient temperature in 5-10 mins yields alcohol (8a) in 63%. Further TEMPO catalyzed oxidation of alcohol (8a) using iodobenzene diacetate in presence of water miscible polar organic solvent such as methanol, acetonitrile (ACN); preferably mixture of ACN:water in (4:1) ratio at room temperature for 3 to 4 hrs is carried to obtain MOM protected carboxylic acid (12) in 80% yield.

The carboxylic acid (12) obtained from the above two methods is further used for the preparation of desired decanolides; preferably Stagonolide C or Modiolide A as described hereinabove.

In another preferred embodiment, the present invention provides organocatalytic process for the asymmetric synthesis of decanolides of Formula Ib.

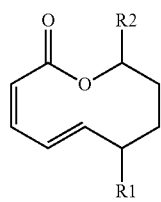

Formula Ib wherein, R1 and R2 are independently selected from —OH or —H, substituted or un-substituted (C₁-C₅) alkyl; (——) bond represents either cis or trans position of the R1 and R2 i.e. (either —— or ⋯⋯).
with the proviso, when R1 is —OH either in cis or trans position; R2 is methyl group either in cis or trans position the compound is Stagonolide E.

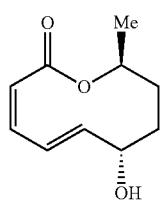

Stagonolide: E

In yet another embodiment the process for the preparation of compound of Formula Ib, preferably Stagonolides E (as shown in scheme 4) comprises the steps of:
a) protecting one of the terminal hydroxyl group of diol (21) to obtain corresponding mono-benzyl ether (22), followed by oxidation to give benzyl protected aldehyde (23);
b) proline catalyzed asymmetric aminoxylating of (23) to obtain chiral diol (24), which is further treated with dibutyl tin oxide and tosyl chloride with subsequent alkaline hydrolysis to give epoxy compound (25);
c) reducing epoxy compound (25) in presence of LAH affords chiral secondary alcohol (26), subsequent protecting with TBS followed by deprotection of benzyl gives alcohol (28); further TEMPO catalyzed oxidizing affords aldehyde compound (29);
d) catalytic HWE olefinating and concomitant copper catalyzed oxidizing of compound (29) gives hydroxyl ester (30), further protecting with MOM gives corresponding protected ester (31);
e) reducing the protected ester (31) to obtain aldehyde (32), followed by Wittig reaction gives corresponding ester (33); further deprotecting of TBS gives secondary alcohol (34), followed by alkali hydrolysis yields corresponding carboxylic acid (35); and
f) macrolactonizing of (35) in presence of 2,4,6 trichloro benzoyl chloride, with subsequent deprotecting of MOM gives desired decanolide compound, preferably Stagonolide E.

Scheme 4:

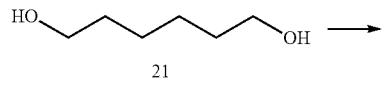

21

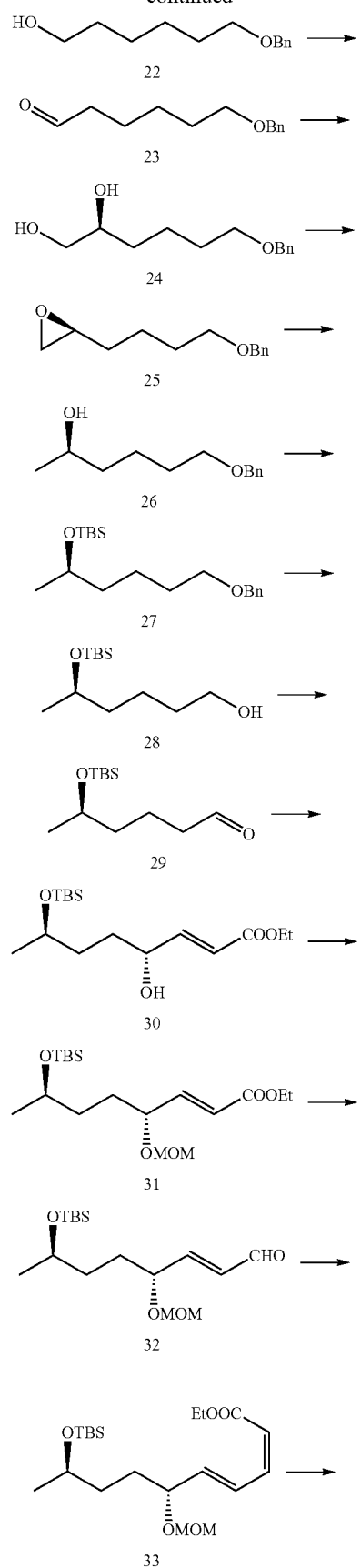

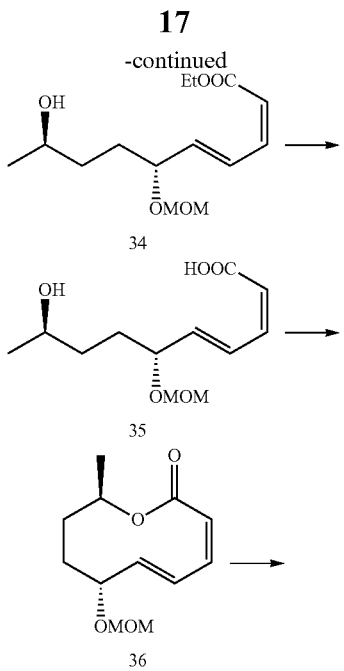

Stagonolide E

Reagents and conditions:
(i) BnBr, NaH, THF, 0-25° C.;
(ii) IBX, DMSO, 25° C. 2 h;
(iii) PhNO, D-proline (20 mol %), -20° C. then MeOH, NaBH$_4$;
(iv) CuSO$_4$, EtOH;
(v) Bu$_2$SnO, TsCl, Et$_3$N, CH$_2$Cl$_2$ then K$_2$CO$_3$, MeOH;
(vi) LiAlH$_4$, THF, 0° C.;
(vii) TBSCl, Imid, CH$_2$Cl$_2$, 0-25° C.;
(viii) H$_2$ (1 atm), 10% Pd/C, Et$_3$N, MeOH; (ix) IBX, DMSO, 25° C.
(viii) L-proline, PhNO, MeCN, -20° C. then triethyl phosphonoacetate, DBU, LiCl then Cu(OAc)$_2$;
(ix) MOMCl, DIPEA, CH$_2$Cl$_2$;
(x) DIBAL-H, dry CH$_2$Cl$_2$, -78° C.;
(xi) Ethyl P,P-bis(2,2,2-trifluoroethyl)phosphonoacetate, dry THF, -78° C.;
(xii) TBAF, THF;
(xiii) LiOH, MeOH/THF/H$_2$O (3:1:1);
(xiv) 2,4,6-trichloro benzoyl chloride, Et$_3$N, THF, 0° C., then DMAP, Toluene, reflux;
(xv) 2N HCl, THF.

In accordance with scheme 4, the substrate 1,6 diol (21) is protected with benzyl group by using benzyl bromide in dry THF to obtain mono-benzyl ether (22), subsequently undergoes to TEMPO catalyzed oxidation in presence of iodobenzene diacetate in organic solvent such as DCM, DMF, affords aldehyde (23). Further the obtained aldehyde on proline-catalyzed direct asymmetric α-aminoxylation using nitrosobenzene in acetonitrile as an oxygen source, followed by treatment with NaBH$_4$ in methanol affords intermediate compound; further obtained compound is treated with copper (II) acetate in methanol for 24 hrs gives the corresponding chiral diol (24). The selective tosylation of the diol (24) using tosyl chloride, triethylamine, and catalytic amount of dibutyltin oxide (Bu$_2$SnO) in DCM furnishes the mono tosylated compound, which is further treated with potassium carbonate in dry methanol at 0° C. for 20-40 mins gives the epoxide (25). Further the epoxide is treated with LAH in dry ether to afford chiral secondary alcohol (26), subsequently the hydroxyl group of (26) is protected by TBS by using TBS-Cl, imidazole in DCM to obtain compound (27), the benzyl group is further cleaved in presence of palladium catalyzed reduction in ethyl acetate gives TBS protected alcohol (28). The obtained alcohol on TEMPO catalyzed oxidation in presence of iodobenzene diacetate in organic solvent yields aldehyde (29). Further the α-aminoxylation of aldehyde (29), is carried out using nitrosobenzene as the electrophilic component followed by in situ Horner-Wadsworth-Emmons olefination with DBU as base that furnishes anilinoxy olefinic ester. The deprotection of anilinoxy group to hydroxyl group is achieved with Cu(OAc)$_2$ in ethanol gives olefin ester (30), further protecting hydroxyl group of (30) in presence of MOMCl and DIPEA in DCM furnishes ester (31). The ester thus formed on reduction by using DIBAL-H in dry DCM at temperature range from -70° C. to -85° C. affords corresponding aldehyde (32), the obtained aldehyde on Wittig reaction in dry THF at temperature range from -70° C. to -85° C. forms ester (33). The TBS group is further cleaved in presence of TBAF in THF to afford (34). Subsequently, hydrolysis of the ester with LiOH in methanol and water yields the corresponding carboxylic acid (35). The acid is further subjected to Yamaguchi macrolactonization conditions i.e. acid (35) is treated with 2,4,6-trichlorobenzoyl chloride and triethylamine in THF, reflux with DMAP, in toluene to afford the MOM protected decanolide (36) further the deprotection of MOM group give rise to desired decanolides i.e Stagonolide-E in high yield, 40% overall and purity, 98% enantiomeric purity.

In yet another embodiment, the present invention provides organocatalytic process for the asymmetric synthesis of 12 member ring macrolide; preferably (6R,11R,14R)-colletallol (as shown in Scheme 4a) which comprises Yamaguchi cyclization of compound (37) and (38) in presence of 2,4,6 trichloro benzoyl chloride, with subsequent deprotecting of MOM and TBS group under the condition as described hereinabove gives desired 12 member ring macrolide i.e. (6R,11R,14R) Colletallol.

Scheme 4a:

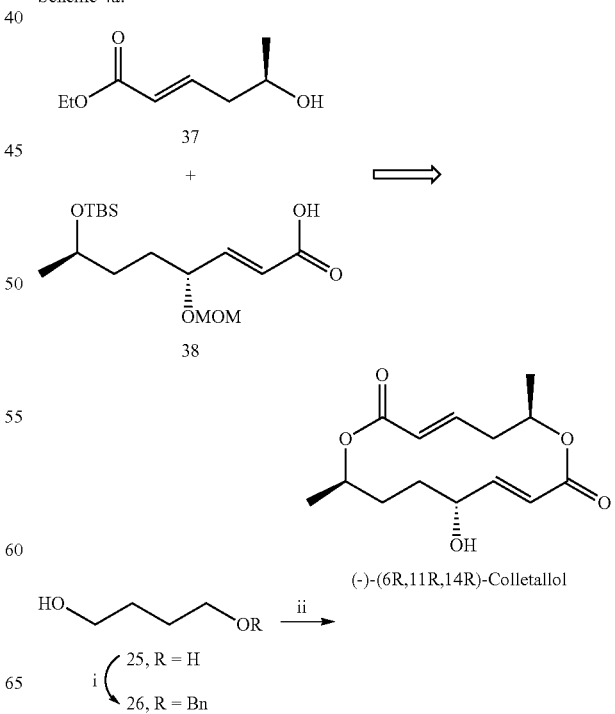

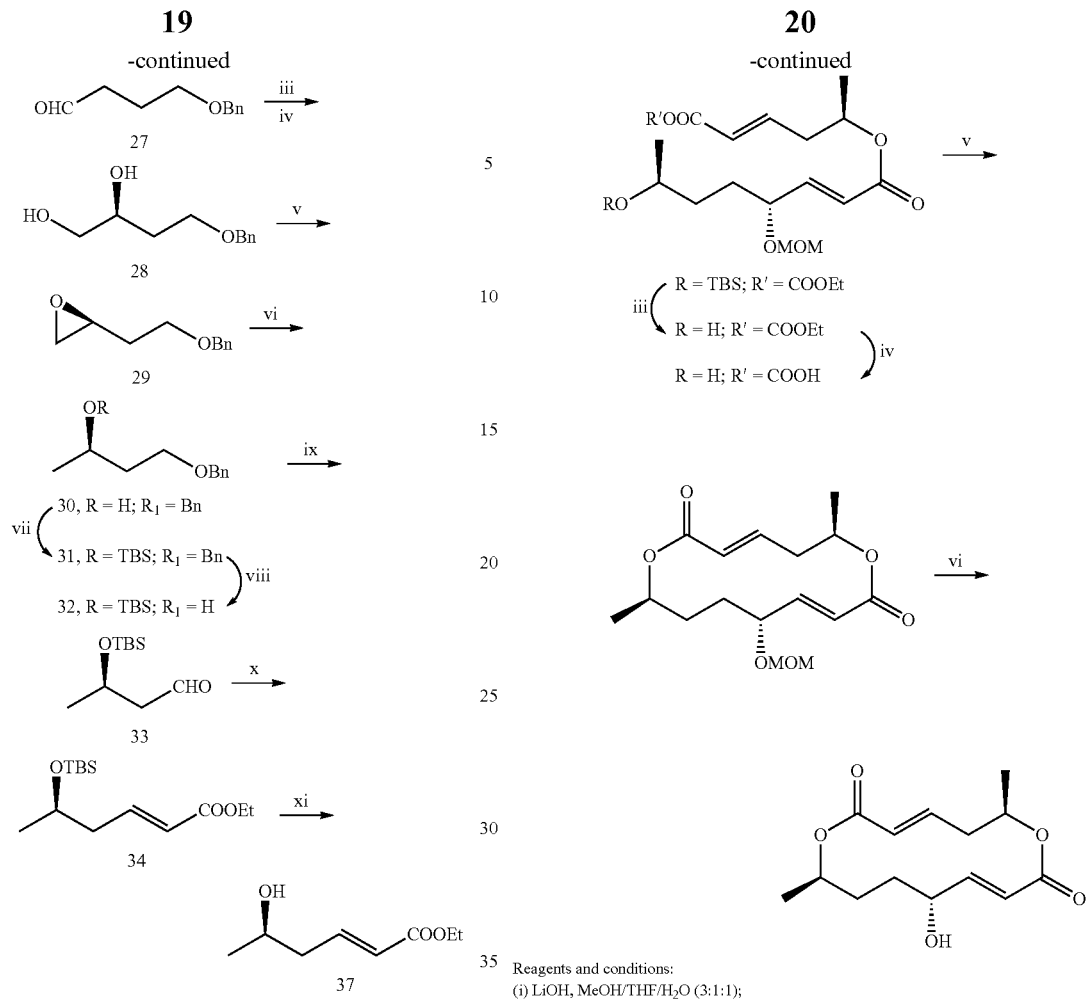
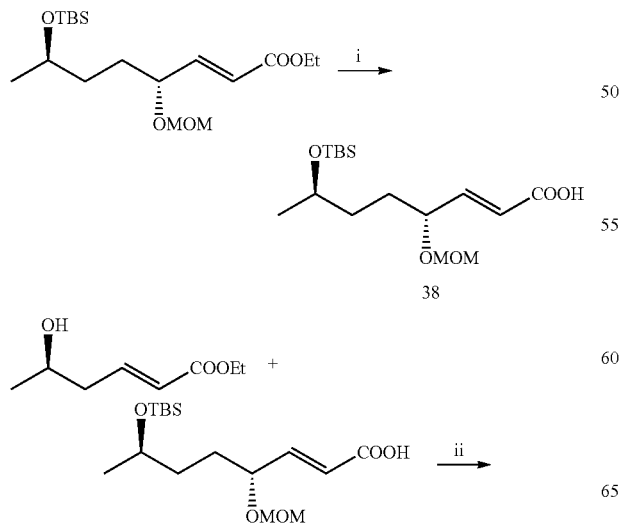
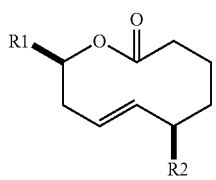

Reagents and conditions:
(i) BnBr, NaH, THF, 0-25° C.;
(ii) IBX, DMSO, 25° C;
(iii) PhNO, D-proline (20 mol %) then MeOH, NaBH$_4$;
(iv) CuSO$_4$, EtOH;
(v) Bu$_2$SnO, TsCl, Et$_3$N, CH$_2$Cl$_2$ then K$_2$CO$_3$, MeOH;
(vi) LiAlH$_4$, THF, 0° C.;
(vii) TBSCl, Imid., CH$_2$Cl$_2$, 0-25° C.;
(viii) H$_2$ (1 atm), 10% Pd/C, Et$_3$N, MeOH, 25° C.;
(ix) IBX, DMSO, 25° C.;
(x) Ph$_3$P=CHCOOEt, CH$_2$Cl$_2$;
(xi) TBAF, THF, rt.

Reagents and conditions:
(i) LiOH, MeOH/THF/H$_2$O (3:1:1);
(ii) DCC, DMAP, CH$_2$Cl$_2$;
(iii) TBAF, THF;
(iv) LiOH, MeOH/THF/H$_2$0 (3:1:1);
(v) 2,4,6-trichloro benzoyl chloride, Et$_3$N, THF, 0° C. then DMAP, Toluene, reflux;
(vi) 2N HCl, THF, rt.

In another preferred embodiment, the present invention provides organocatalytic process for the asymmetric synthesis of decanolides of Formula Ic.

wherein, R1 and R2 is independently selected from the group consisting of H, OH, substituted or unsubstituted (C$_1$-C$_5$) alkyl; (———) represents cis or trans position of R1 and R2 i.e. (either ━━ or ″″″″);

with the proviso, when, R1 is methyl either in cis or trans position; R2 is —OH on the opposite position with regard to R1 the compound is Stagonolide-F; and

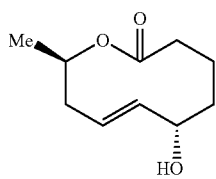

Stagonolide: F with the proviso, when, R1 is methyl either in cis or trans position; R2 is —OH on the same position with regard to R1 the compound is Aspinolide A; and Aspinolide: A In yet another embodiment, the present invention provides organocatalytic process for the preparation of compound of Formula Ic, preferably Stagonolide F and Aspinolide A (as shown in scheme 5) comprises the steps of:

a) enantioselective allylboration of aldehyde (1), to obtain chiral allylic sec alcohol (3);
b) esterification of allylic sec alcohol (3) with TBS protected carboxylic acid (15) with subsequent deprotection to give allylic alcohol (17); and
c) ring closing metathesis reaction of compound (17) in presence of Grubbs II catalyst, gives the desired dacanolides such as Stagonolide F or Aspinolide A (In stagonolide F the OH group and methyl are trans)

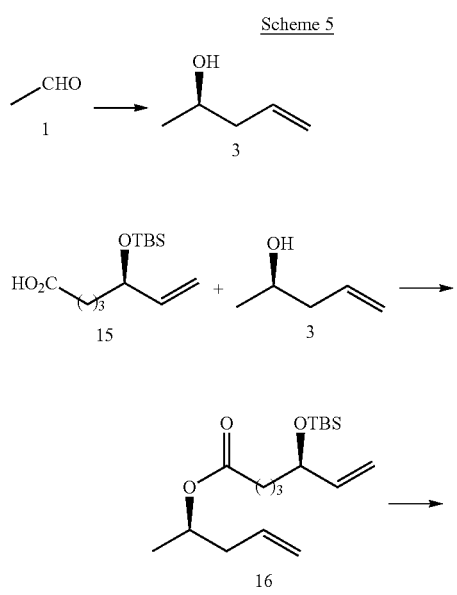

Scheme 5

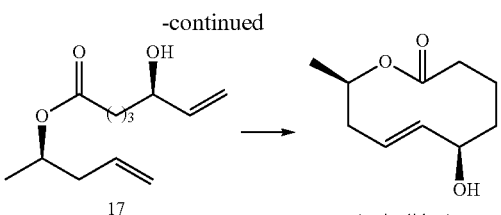

Reagents and conditions:
(i) EDCI·HCl, Et₃N, CH₂Cl₂, 0-25° C., 6 h, 88%;
(ii) (a) TBAF, THF, 2 h; (b) Grubbs-II (10 mol %), dry CH₂Cl₂, reflux, 24 h, 69% (two steps).

In accordance with scheme 5, the aldehyde compound (1) undergoes enantioselective allylboration in presence of allyldiisopinocamphenylborane at temperature in the range of −120° C. to −80° C. for 1-2 hrs in non-polar organic solvents such as, diethyl ether, pentane, cyclopentane, benzene, toluene, 1,4-dioxane, chloroform or mixtures thereof preferably mixture of diethyl ether-pentane, followed by treatment with NaOH and aqueous $H_2O_2$ to obtain chiral allylic alcohol (3) in 71% yield with 99% ee.

The carboxylic acid (15) on esterification with allylic alcohol (3) in presence of EDCl HCl, DMAP in DCM at temperature range 0° to 30° C. for 5 to 8 hrs affords 86% yield of compound (16), followed by deprotection of TBS in presence of TBAF in THF for 6-8 hrs gives allylic alcohol (17) in 82% yield. Further the ring closing metathesis reaction of allylic alcohol (17) in presence of Grubbs II catalyst (5 to 15%) in dry DCM for 24 hrs yields 62% of desired decanolides i.e. Aspinolide-A.

In another embodiment, the chiral allylic alcohol (3) can be prepared from ethyl acetoacetate (41) as described in scheme 6:

Scheme 6:

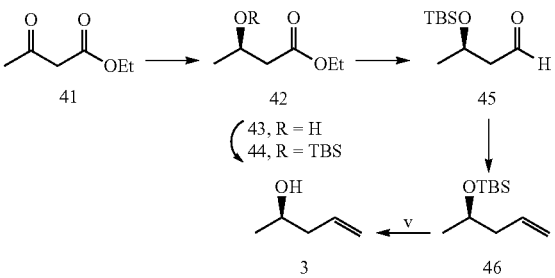

Reagents and conditions:
(i) [(R)-Ru(BINAP)Cl₂]₂· NEt₃ (0.1 mol %), 2N HCl (0.1 mol %), MeOH, H₂(100 psi) 50° C.;
(ii) TBSCl, imid., CH₂Cl₂, 0-25° C.;
(iii) DIBAL-H. toluene, -78° C.;
(iv) Ph₃PCH₃I, nBuLi, THF;
(v) TBAF, THF.

In accordance with scheme 6, Noyori asymmetric hydrogenation of ethyl aceoacetate (41) in presence of 0.1% of BINAP-Ru dichloride, NEt3 (0.1 mol %), 2N HCl (0.1 mol %), MeOH, H₂ (100 psi) gives chiral hydroxy ester (43) in 95% yield with 98% ee. followed by protection of hydroxy group in presence of TBS-Cl, imidazole in DCM at temperature range 0° C. to 30° C. for 1 to 3 hrs affords TBS protected ester (44) in 97% yield, which on further reduction in presence of DIBAL-H in toluene at temperature ranging from −70° to −80° C. for 0.5 to 2 hrs yields 85% of aldehyde (45) which on Wittig reaction in presence of n-BuLi, Ph₃P=CH₃I in dry THF at temperature range −50° to room temperature for 2-4 hrs gives the olefin (46) in 73% yield, the subsequent deprotection of TBS in presence of TBAF in THF at temperature range −5° C. to 0° C. for 1-3 hrs affords allylic alcohol (3) in 81% yield.

In another embodiment the TBS protected carboxylic acid (15) can be synthesized by two methods. The first method for the preparation of TBS protected carboxylic acid (15) is illustrated in scheme 7.

Scheme 7:

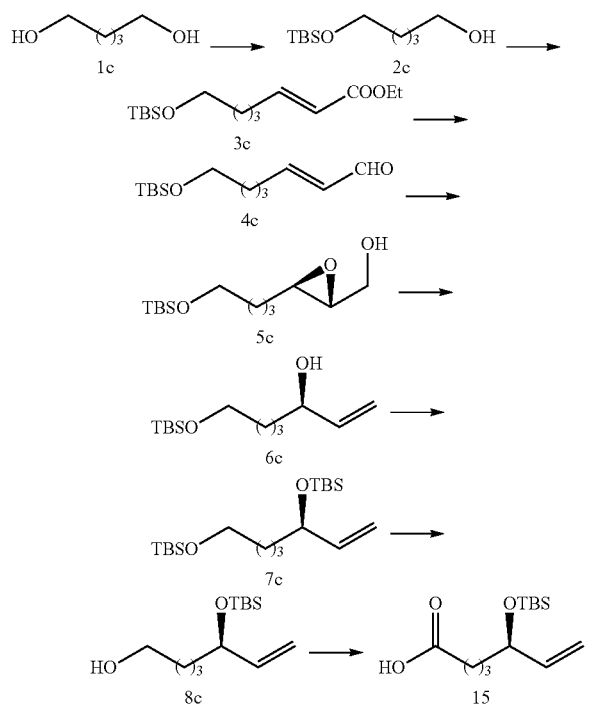

Reagents and conditions:
(i) TBSCl, Imid, CH₂Cl₂, 0-25° C.;
(ii) IBX, DMSO, 25° C.;
(iii) Ph₃P = CHCOOEt, CH₂Cl₂;
(iv) DIBAL-H, toluene. -78° C.;
(v) H₂O₂, CH₂Cl₂,
(S)-2-[bis(3,5-trifluoromethylphenyl)tri-methylsilanyloxymethyl]pyrrolidine, 25° C., 4 h then NaBH₄, MeOH, 0° C., 1 h, 43%;
(vi) (a) I₂, PPh₃, imid., Et₂O/CH₃CN (3:1), 0-25° C., 2 h, 90%; (b) Zn, NaI, MeOH, reflux, 3 h, 90%;
(vii) TBSCl, imid, CH₂Cl₂, 0-25° C., 6 h, 86%;
(viii) CSA, MeOH, 25° C., 5 min., 63%;
(ix) TEMPO, PhI(OAc)₂, CH₃CN: H₂O (4:1), 25° C., 4 h, 80%.

In accordance with scheme 7, the TBS protected carboxylic acid (15) can be synthesized from 1,5 diol (1c), followed by the similar steps as described hereinabove in scheme 2.

The second method for the preparation of TBS protected carboxylic acid (15) is illustrated in scheme 8.

Scheme 8:

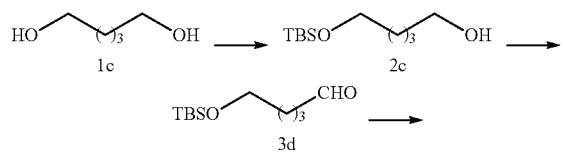

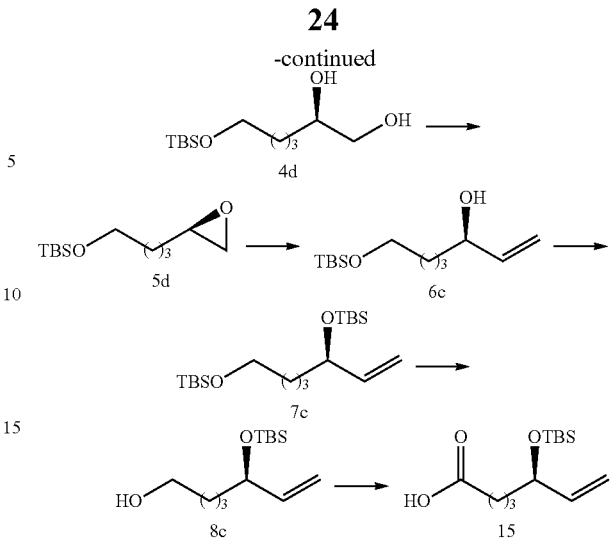

Reagents and conditions:
(i) TBSCl, Imid, CH₂Cl₂, 0-25° C., 95%;
(ii) IBX, DMSO, 25° C., 90%;
(iii) (a) PhNO (0.9 equiv.), D-proline (20 mol %), CH₃CN, -20° C., 24 h then NaBH₄, MeOH, 0° C., 1 h; (b) Cu(OAc)₂, MeOH, 24 h, 60% (over two steps);
(iv) (a) TsCl, ET₃N, Bu₂SnO, DMAP; (b) K₂CO₃, MeOH, 30 min., 92%;
(v) (CH₃)₃S(O)I, NaH, DMSO, 25° C. 2 h, 70%;
(vi) TBSCl, DIPEA, dry CH₂Cl₂, 16 h, 90%;
(v) TBAF, THF, 2 h, 82%;
(vii) TEMPO, PhI(OAc)₂, CH₃CN: H₂O (4:1), 25° C., 4 h, 80%.

In accordance with scheme 8, the TBS protected carboxylic acid (15) can be synthesized from 1,5 diol, followed by the similar steps as described hereinabove in scheme 3.

In an embodiment, the present invention provides the spectral data for the intermediate compounds synthesized by the process described above. Accordingly, the IR spectra are recorded on an FT-IR spectrometer. The ¹H and ¹³C NMR spectra are recorded on 200/400/500 MHz and 50/100/125 MHz NMR spectrometer respectively in CDCl3/CD3OD/DMSO-d6 solvents.

In an embodiment, the compound Decanolides of the instant are used as anti-bacterial, anti-fungal and phytotoxic agents.

The following examples are given by way of illustration of the present invention and therefore should not be construed to limit the scope of the invention.

EXAMPLES

Example 1: Compound of Formula 2c; 5-((tert-butyldimethylsilyl)oxy)pentan-1-ol

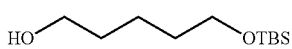

To a solution of 1,5-pentane diol in dry CH₂Cl₂ at 0° C. was added imidazole (1.5 equiv.) and tert-butyldimethylsilyl chloride (1.2 equiv). The reaction mixture was stirred at 25° C. for 2 h. After completion of reaction (monitored by TLC), it was diluted with CH₂Cl₂, washed with water, brine and dried over anhydrous Na₂SO₄. Removal of solvent under reduced pressure gave the crude product which was further purified by column chromatography to yield 2c as a colorless liquid.

IR (CHCl₃): 760, 835, 1090, 1255, 1463, 2935, 3354 cm⁻¹; ¹H NMR (200 MHz, CDCl₃): δ 0.02 (s, 6H), 0.87 (s,

9H), 1.38-1.67 (m, 6H), 1.7 (brs, 1H), 3.56-3.64 (m, 4H); $^{13}$C NMR (50 MHz, CDCl$_3$): δ −5.2, 18.4, 22.1, 26.0, 32.8, 62.8, 63.1.

Example 2: Compound of Formula 3b; 5-((tert-butyldimethylsilyl)oxy)pentanal

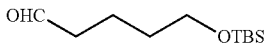 [SMILES: CC(C)(C)[Si](C)(C)OCCCCC=O]

To a well stirred solution of 2c in dry CH$_2$Cl$_2$ at 0° C. were added (diacetoxyiodo)benzene (1.1 equiv) and TEMPO free radical (0.1 equiv). The reaction mixture was warmed to room temperature and stirred for 1 h. The reaction mixture was quenched with saturated solution of sodium thiosulphate solution, the aqueous mixture was extracted with CH$_2$Cl$_2$. The organic layer was washed with saturated NaHCO$_3$ solution and brine and dried over anhydrous Na$_2$SO$_4$. Evaporation of the solvent provided aldehyde 3b a colorless liquid.

IR (CHCl$_3$): 777, 837, 1047, 1257, 1472, 1720, 2858, 2955 cm$^{-1}$; $^1$H NMR (200 MHz, CDCl$_3$): δ 0.04 (s, 6H), 0.89 (s, 9H), 1.54-1.75 (m, 4H), 2.42-2.50 (m, 2H), 3.58 (t, J=6.1 Hz, 2H); $^{13}$C NMR (50 MHz, CDCl$_3$): δ −5.3, 18.3, 18.6, 25.9, 32.11, 43.6, 62.5.

Example 3: Compound of Formula 4b; (S)-5-((tert-butyldimethylsilyl)oxy)pentane-1,2-diol

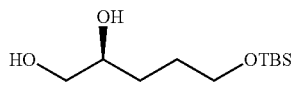

To a stirred precooled (−20° C.) acetonitrile solution of aldehyde 3b and nitrosobenzene (1.0 equiv.) D-proline (20 mol %) was added. The reaction mixture was allowed to stir at the same temperature for 24 h followed by the addition of methanol and NaBH$_4$ (2.0 equiv.) to the reaction mixture, which was stirred for 10 min After addition of phosphate buffer, the resulting mixture was extracted with EtOAc and the combined organic phases were dried over anhydrous. Na$_2$SO$_4$ and concentrated to give the crude aminoxy alcohol which was directly taken up for next step without further purification. To a MeOH solution of the crude aminoxy alcohol was added 10% Pd/C & stirred under H$_2$ (1 atm.) at 25° C. for 24 h. After completion of reaction (monitored by TLC), it was filtered over celite plug (MeOH eluent) and solvent evaporated under reduced pressure to give the corresponding diol as a colourless oil.

IR (CHCl$_3$): 668, 775, 835, 1006, 1097, 1256, 1463, 1471, 2857, 2929, 2954, 3361 cm$^{-1}$; $^1$H NMR (200 MHz, CDCl$_3$): δ 0.02 (s, 6H), 0.83 (s, 9H), 1.37-1.67 (m, 4H), 2.42 (brs, 1H), 3.35-3.86 (m, 6H); $^{13}$C NMR (50 MHz, CDCl$_3$): δ −5.35, 18.32, 25.94, 28.98, 30.04, 63.31, 66.63, 71.98.

Example 4: Compound of Formula 5b; (S)-tert-butyldimethyl(3-(oxiran-2-yl)propoxy)silane

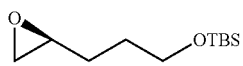 [SMILES: CC(C)(C)[Si](C)(C)OCCC[C@H]1CO1]

A solution of diol 4b in CH$_2$Cl$_2$ was treated with tosyl chloride (1.1 equiv) and triethylamine (2.0 equiv) at 0° C. After being stirred for 15 min, the mixture was extracted with CH$_2$Cl$_2$, washed with water & combined organic phases were dried over anhyd. Na$_2$SO$_4$ and concentrated to give the crude tosylate, which was purified by column chromatography over silica gel to give epoxide 5b as a colourless oil.

IR (CHCl$_3$): 776, 836, 938, 965, 1006, 1101, 1255, 1463, 1471, 2857, 2955, 2955 cm$^{-1}$; $^1$H NMR (200 MHz, CDCl$_3$): δ 0.04 (s, 6H), 0.89 (s, 9H), 1.57-1.71 (m, 4H), 2.44-2.48 (dd, J=7.1 Hz, 3H), 2.46 (br.s, 1H), 3.60-3.73 (m, 3H), 4.17-4.28 (m, 3H), 6.07 (d, J=15.7 Hz, 1H), 6.82-6.93 (m, 1H); $^{13}$C NMR (50 MHz, CDCl$_3$): δ −5.29, 18.34, 25.97, 29.05, 46.98, 52.06, 62.57.

Example 5: Compound of Formula 6a: (S)-6-((tert-butyldimethylsilyl)oxy)hex-1-en-3-ol To a stirred solution of trimethylsulfonium iodide (7.98 g, 39.12 mmol) in dry DMSO (90 mL) was added NaH (1.38 g, 60.18 mmol) at 25° C. After 30 min, epoxide 5b (6.5 g, 30.09 mmol) in dry DMSO (15 mL) was introduced dropwise and the reaction mixture stirred for 2 h. After completion of the reaction as monitored by TLC, it was quenched with water and extracted with diethyl ether (3×100 mL). The combined extracts were washed with brine, dried over anhydrous. Na$_2$SO$_4$ and concentrated under reduced pressure. The crude product was then purified by column chromatography using petroleum ether/EtOAc (8:2 v/v) to give allylic alcohol (6.0 g) as a colorless liquid.

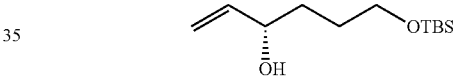

IR (CHCl$_3$): 692, 776, 837, 939, 969, 1005, 1104, 1255, 1361, 1388, 1443, 1471, 2956, 3354 cm$^{-1}$; $^1$H NMR (200 MHz, CDCl$_3$): δ 0.02 (s, 6H), 0.84 (s, 9H), 1.54-1.60 (m, 4H), 2.61 (br s, 3H), 3.56-3.62 (t, J=6 Hz 2H), 4.06 (m, 1H), 4.99-5.23 (m, 2H), 5.71-5.88 (m, 1H); $^{13}$C NMR (50 MHz, CDCl$_3$): δ −5.32, 18.38, 26.00, 28.77, 34.42, 63.37, 72.59, 114.30, 141.29.

Example 6: Compound of Formula 7a: (S)-10,10,11,11-tetramethyl-5-vinyl-2,4,9-trioxa-10-siladodecane

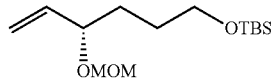

To allylic alcohol 6a in CH$_2$Cl$_2$ at 0° C. were successively added DIPEA (3.0 equiv), DMAP (120 mg), and MeOCH$_2$Cl (2.2 equiv). The resulting mixture was stirred for 3 h at r.t. (25° C.) the reaction quenched by adding H$_2$O (10 ml), and the mixture extracted with CH$_2$Cl$_2$. The organic extracts were washed with brine (10 ml), dried (anhy. Na$_2$SO$_4$) and concentrated. The crude was purified by column chromatography.

IR (CHCl$_3$): 775, 835, 1037, 1097, 1257, 1474, 2857, 2929, 2953, cm$^{-1}$; $^1$H NMR (200 MHz, CDCl$_3$): δ 0.04 (s, 6H), 0.90 (s, 9H), 1.57-1.66 (m, 4H), 3.36 (s, 3H), 3.59-3.65

(t, J=6, Hz 2H), 3.97-4.0 (m, 1H), 4.50-4.53 (d, J=3 Hz, 1H), 4.67-4.70 (d, J=3 Hz, 1H), 5.15-5.24 (m, 2H), 5.57-5.75 (m, 1H); $^{13}$C NMR (50 MHz, CDCl$_3$): δ −4.59, 19.03, 26.67, 29.32, 32.38, 55.99, 63.56, 94.27, 117.86, 139.08.

Example 7: Compound of Formula 8a: (S)-4-(methoxymethoxy)hex-5-en-1-ol

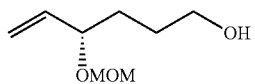

To a compound 7a in dry THF was added dropwise 1 M solution of tetrabutylammonium fluoride (2 equiv.) at 25° C. and stirred at this temperature for 6 h. After completion of reaction (monitored by TLC) the solvent was removed under reduced pressure and the residue extracted with ethyl acetate. The organic layer was washed with water, brine and dried over anhydrous Na$_2$SO$_4$. The crude product was subjected to flash column chromatography to afford the primary alcohol 8a as a colourless liquid.

IR (CHCl$_3$): 1097, 1643, 1447, 2933, 3415 cm-1; $^1$H NMR (200 MHz, CDCl$_3$): 1.58-1.74 (m, 4H), 1.85 (br.s, 1H), 3.37 (s, 3H), 3.66 (t, J=6.04, Hz, 2H), 4.01 (q, J=5.28, 12.8 Hz, 2H), 4.51 (d, J=6.79 Hz, 1H), 4.68 (d, J=6.79 Hz, 1H), 5.17 (br.s, 1H), 5.23 (d, J=7.55 Hz, 1H), 5.68 (m, 1H); $^{13}$C NMR (50 MHz, CDCl$_3$): δ 28.32, 31.61, 55.25, 62.19, 77.05, 93.46, 177.22, 137.90.

Example 8: Compound of Formula 12: (S)-4-(methoxymethoxy)hex-5-enoic acid

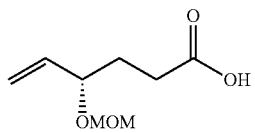

To a MOM protected primary alcohol (450 mg) in CH$_3$CN: H$_2$O (4:1) were added (diacetoxyiodo)benzene (1.2 g) and TEMPO free radical (86.3 mg) at 25° C. and stirred at this temperature for 4 h. After completion of reaction (monitored by TLC) the solvent was removed under reduced pressure and the residue extracted with ethyl acetate. The organic layer was washed with water, brine and dried over anhydrous Na$_2$SO$_4$. The crude product was subjected to flash column chromatography to afford the acid 12 as a colourless liquid. Yield 86%.

IR (CHCl$_3$): 920, 1029, 1096, 1149, 1255, 1424, 1255, 1149, 1255, 1424, 1711, 2888, 2937, 3447 cm$^{−1}$; $^1$H NMR (200 MHz, CDCl$_3$): 1.86 (q, J=6.79, 13.59 Hz, 2H), 2.46 (t, J=6.79 Hz, 2H), 3.36 (s, 3H), 4.02 (q, J=6.79, 13.59 Hz, 2H), 4.49 (d, J=6.79 Hz, 1H), 4.65 (d, J=6.79 Hz 1H), 5.19 (d, J=7.55 Hz, 1H), 5.24 (d, J=7.55 Hz, 1H), 5.66 (m, 1H); $^{13}$C NMR (50 MHz, CDCl$_3$): δ 29.42, 30.1, 54.89, 75.7393.12, 117.32, 136.90, 178.71.

Example 9: (R)-Ethyl (−)-3-hydroxybutyrate, (43)

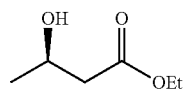

Ethyl acetoacetate (7.5 g) and dry methanol (25 mL) were mixed and deoxygenated with flowing nitrogen for five minutes. The catalyst [(R)—Ru(BINAP)Cl$_2$]$_2$.NEt3 (0.1 mol %) was added along with 2N HCl (0.1 mol %). The mixture was transferred to a standard Parr reactor apparatus and flushed by evacuating and refilling with hydrogen several times. The apparatus was heated at 50° C. with stirring under 100 psi of hydrogen for 16 h. After completion of reaction (monitored by TLC) the reaction was cooled and concentrated under reduced pressure. The residue was subjected to column chromatographic purification with petroleum ether/ethyl acetate (9:1 v/v) to get pure (R)-alcohol 43 as a colorless liquid.

$[α]_D^{25}$ −46.0 (c 1.0, CHCl$_3$); $[α]_D^{25}$ −46.0 (c 1.0, CHCl$_3$); 98% ee (Mosher ester); IR (CHCl$_3$, cm$^{−1}$) 3441.7, 2978.6, 2935.7, 1734.0, 1636.1, 1458.1; $^1$H NMR (200 MHz, CDCl$_3$): δ 4.12-4.22 (m, 3H), 3.20 (d, J=3.8 Hz, 1H), 2.42-2.45 (m, 2H), 1.21-1.31 (m, 6H); $^{13}$C NMR (50 MHz, CDCl$_3$): δ 172.5, 64.2, 60.5, 43.2, 22.6, 14.1. Analysis: C$_6$H$_{12}$O$_3$ requires C, 54.53; H, 9.15. found C, 54.56; H, 9.35%.

Example 10: (R)-(−)-Ethyl (tert-butyldimethyl silyloxy)butyrate, (44)

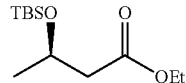

To a solution of ethyl (R)-(−)-3-hydroxybutyrate 43 in dry CH$_2$Cl$_2$ at 0° C. was added imidazole (1.5 equiv) and tert-butyldimethylsilyl chloride (1.2 equiv.). The reaction mixture was stirred at 25° C. for 2 h. After completion of reaction (monitored by TLC), it was diluted with CH$_2$Cl$_2$, washed with water, brine and dried over anhydrous Na$_2$SO$_4$, Concentration and purification by column chromatography with petroleum ether/ethyl acetate (49:1 v/v) gave aldehyde 44 as a colorless liquid.

$[α]_D^{25}$ −26.0 (c 1.0, CH$_2$Cl$_2$); lit.$^{12}$ $[α]_D^{25}$ −25.5 (c 1.0, CH$_2$Cl$_2$); IR (CHCl$_3$ cm$^{−1}$) 2958, 2931, 2897, 2857, 1739, 1473, 1447; $^1$H NMR (200 MHz, CDCl$_3$): δ 4.19-4.28 (m, 1H), 4.13 (q, J=7.2 Hz, 2H), 2.44 (dd, J=7.4, 14.5 Hz, 1H), 2.32 (dd, J=5.4, 14.5 Hz, 1H), 1.22 (t, J=7.2 Hz, 3H), 1.17 (d, J=6.1 Hz, 3H), 0.82 (s, 9H), δ 0.05 (s, 3H), δ 0.04 (s, 3H); $^{13}$C NMR (50 MHz, CDCl$_3$): δ171.2, 65.8, 59.9, 44.8, 25.7, 23.9, 17.9, 14.2, −4.5, −5.0. Analysis: C$_{12}$H$_{26}$O$_3$Si requires C, 58.49; H, 10.63 found C, 58.54; H, 10.56%.

Example 11: (R)-(−)-Ethyl (tert-butyldimethylsilyloxy)butanal, (45)

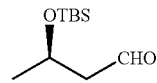

To a stirred solution of ester 44 in dry toluene (250 mL), a solution of diisobutylaluminium hydride (1.0 equiv.), 1M in cyclohexane was added dropwise at −78° C. and stirred at said temperature for 1 h. After completion of reaction (monitored by TLC), it was diluted with a saturated solution of Rochelle salt (1 g) and stirred for further 3 h. The organic phase was separated and the aqueous phase extracted twice with CH$_2$Cl$_2$. The combined organic phase was washed with water, brine and dried over anhydrous Na$_2$SO$_4$. Removal of solvent under reduced pressure and column chromatographic purification with petroleum ether/ethyl acetate (19:1 v/v) gave aldehyde 45 as a colorless liquid.

[α]$_D^{25}$ −13.6 (c 1.6, CH$_2$Cl$_2$); lit.[12] [α]$_D^{25}$ −11.3 (c 1.0, CH$_2$Cl$_2$); IR (CHCl$_3$, cm$^{−1}$) 2957, 2930, 2896, 2858, 1729, 1473, 1463, 1377, 1362; $^1$H NMR (200 MHz, CDCl$_3$): δ 9.76 (dd, J=2.1, 2.7 Hz, 1H), 4.25-4.40 (m, 1H), 2.40-2.59 (m, 2H), 1.19 (d, J=6.2 Hz, 3H), 0.84 (s, 9H), 0.08 (s, 3H), 0.06 (s, 3H); $^{13}$C NMR (50 MHz, CDCl$_3$): δ 202.0, 64.5, 52.9, 25.7, 24.1, 17.9, −4.4, −5.0. Analysis: C$_{10}$H$_{22}$O$_2$Si requires C, 59.35; H, 10.96. found C, 59.38; H, 10.97%.

Example 12: (R,E)-Ethyl 5-(tert-butyldimethylsilyloxy)hex-2-enoate (5)

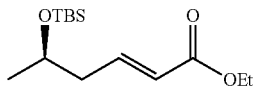

To a solution of aldehyde 4 in dry THF (200 mL) at 25° C. was added Ph$_3$P=CHCOOEt (2.0 equiv.) and the reaction mixture was stirred for 12 h. After completion of reaction (monitored by TLC), solvent was distilled off under reduced pressure and the crude mass on flash chromatographic purification gave the α,β-unsaturated ester 5 as a colourless liquid.

IR (CHCl$_3$, cm$^{−1}$) 775, 836, 1003, 1045, 1093, 1132, 1175, 1222, 1258, 1317, 1723; $^1$H NMR (200 MHz, CDCl$_3$): δ 0.04 (s, 6H), 0.88 (s, 9H), 1.14 (d, J=6.61 Hz 3H), 1.25 (t, J=6.61 Hz, 3H), 2.23-2.31 (m, 2H), 3.80-3.95 (m, 1H), 4.09-4.19 (q, J=7.03, 14.06 Hz 2H), 5.73-5.80 (d, J=15.81 Hz, 1H), 6.81-6.97 (m, 1H); $^{13}$C NMR (50 MHz, CDCl$_3$): δ −4.18, −4.50, 14.30, 18.09, 23.83, 25.83, 42.46, 60.00, 67.64, 123.25, 145.85, 166.17.

Example 13: (R,E)-Ethyl 5-(tert-butyldimethylsilyloxy)hex-2-enoate 6

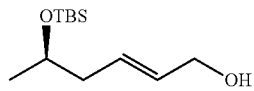

To a stirred solution of ester 5 in dry toluene (250 mL), a solution of diisobutylaluminium hydride (2.0 equiv., 1M in cyclohexane) was added dropwise at −78° C. and stirred at this temperature for 1 h. After completion of reaction (monitored by TLC), it was diluted with a saturated solution of Rochelle salt and stirred for further 3 h. The organic phase was separated and the aqueous phase extracted twice with CH$_2$Cl$_2$. The combined organic phase was washed with water, brine and dried over anhydrous Na$_2$SO$_4$. Removal of solvent under reduced pressure and flash chromatographic purification gave 6 as a colorless liquid.

IR (CHCl$_3$, cm$^{−1}$) 690, 775, 840, 940, 972, 1010, 1103, 1253, 1361, 1387, 1442, 1468, 2950, 3348; $^1$H NMR (200 MHz, CDCl$_3$): δ 0.04 (s, 6H), 0.90 (s, 9H), 1.11 (d, J=6.86 Hz 3H), 2.11-2.23 (m, 2H), 3.61-3.86 (m, 1H), 4.02-4.11 (m, 2H), 5.60-5.65 (m, 2H); $^{13}$C NMR (50 MHz, CDCl$_3$): δ −3.95, −4.58, 18.33, 26.25, 42.90, 60.76, 64.06, 68.75, 129.97, 131.65.

Example 14: (R,E)-Ethyl 5-(tert-butyldimethylsilyloxy)hex-2-enoate (7)

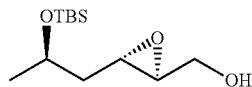

The catalyst (R)-α,α-Bis[3,5-bis(trifluoromethyl)phenyl]-2-pyrrolidinemethanol tri-methylsilyl ether (1.2 g, 10 mol %) was added at ambient temperature to a solution of aldehyde (4.5 g, 19.73 mmol) in CH$_2$Cl$_2$ (60 mL) followed by the addition of 35% H$_2$O$_2$ (aq.) (1.3 equiv.). After the completion of reaction (monitored by TLC), it was diluted with MeOH (60 mL) and cooled to 0° C. followed by addition of NaBH$_4$ (1.49 g, 39.47 mmol). The mixture was then stirred for 10 min, quenched with sat. NH$_4$Cl and extracted with CH$_2$Cl$_2$. The organic layer was separated, dried over anhydrous Na$_2$SO$_4$ and the solvent removed under reduced pressure. The crude product was purified by column chromatography with petroleum ether/EtOAc (8:2 v/v) to give epoxy alcohol (2.57 g) as a colourless liquid.

IR (CHCl$_3$, cm$^{−1}$) 775, 836, 1006, 1050, 1072, 1130, 1256, 2857, 2929, 2956, 3437; $^1$H NMR (200 MHz, CDCl$_3$): δ 0.08 (s, 6H), 0.89 (s, 9H), 1.16 (d, J=6.86 Hz 3H), 1.44-1.56 (m, 1H), 1.67-1.81 (m, 2H), 2.89-2.93 (m, 1H), 3.02-3.09 (m, 1H), 3.54-3.66 (m, 1H), 3.88-4.07 (m, 2H); $^{13}$C NMR (50 MHz, CDCl$_3$): δ −4.87, −4.45, 18.02, 24.32, 25.82, 41.82, 53.39, 58.82, 61.50, 66.23.

Example 15: (R,E)-Ethyl 5-(tert-butyldimethylsilyloxy)hex-2-enoate (9)

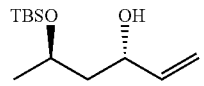

To a stirred solution of epoxy alcohol (2.5 g, 10.14 mmol) in dry ether-acetonitrile mixture (3:1, 40 ml) at 0° C. under nitrogen atmosphere were added imidazole (1.03 g, 15.21 mmol), triphenylphosphine (3.98 g, 15.21 mmol) and iodine (4.61 g, 18.25 mmol) successively. The resulting reaction mixture was stirred for 1 h at the same temperature and then diluted with cold ether (20 mL), and filtered through a sintered funnel. The residue was washed with ether (3×50 mL), dried over anhydrous Na$_2$SO$_4$ and concentrated in vacuo. Purification of the crude residue by column chromatography (9:1 v/v) gave the pure product epoxy iodide (3.5 g) as a pale yellow liquid.

A mixture of the above epoxy iodide (3.47 g, 9.74 mmol), NaI (3.62 g, 24.36 mmol) and freshly activated zinc (0.126 g, 1.94 mmol) in dry MeOH (45 ml) was refluxed for 6 h under nitrogen atmosphere. The solution was filtered and the residue washed with MeOH (2×25 mL). The combined filtrates were concentrated and the residue was taken in ethyl acetate (50 mL), washed with water (2×25 mL), brine (3×50 mL), dried over anhydrous Na$_2$SO$_4$ and concentrated undered reduced pressure. The crude compound was purified by column chromatography using petroleum ether/EtOAc (8:2 v/v) to afford the allyl alcohol (2.0 g) as a colorless oil.

IR (CHCl$_3$, cm$^{−1}$) 775, 836, 1040, 1078, 1128, 1255, 2856, 2929, 2957, 3441; $^1$H NMR (200 MHz, CDCl$_3$): δ

0.09 (s, 6H), 0.90 (s, 9H), 1.22 (d, J=6.67 Hz 3H), 1.59-1.67 (m, 2H), 3.21 (br.s, 1H), 4.15-4.27 (m, 1H), 4.38-4.46 (m, 1H), 5.04-5.29 (m, 2H), 5.77-5.93 (m, 1H); $^{13}$C NMR (50 MHz, CDCl$_3$): δ −4.89, −4.31, 18.01, 23.19, 25.89, 44.57, 67.10, 69.95, 113.84, 141.22.

Example 16: (R,E)-Ethyl 5-(tert-butyldimethylsilyloxy)hex-2-enoate (10)

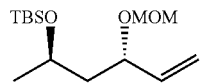

MOM protection procedure same as above. (example no. 6)

$^1$H NMR (200 MHz, CDCl$_3$): δ 0.06 (s, 6H), 0.89 (s, 9H), 1.44 (d, J=6.99 Hz 3H), 1.59-1.67 (m, 2H), 3.37 (s, 3H), 3.89-4.14 (m, 2H), 4.52-4.69 (dd, J=6.92, 29.08 Hz 2H), 5.13-5.22 (m, 2H), 5.61-5.81 (m, 1H); $^{13}$C NMR (50 MHz, CDCl$_3$): δ −4.89, −4.31, 18.01, 23.19, 25.89, 44.57, 67.10, 69.95, 113.84, 141.22.

Example 17: (2R,4S)-4-(methoxymethoxy)hex-5-en-2-ol (11)

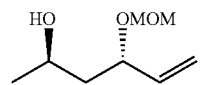

TBS deprotection procedure same as above (example no. 7) [α]$_D^{25}$ −108.6 (c 1.6, CH$_2$Cl$_2$); lit.$^{12}$ [α]$_D^{25}$ −109.2 (c 1.50, CHCl$_3$); IR (CHCl$_3$, cm$^{-1}$) 1037, 1099, 1153, 1597, 2925, 3433; $^1$H NMR (200 MHz, CDCl$_3$): δ 1.18 (d, J=6.20 Hz 3H), 1.63-1.72 (m, 2H), 2.56 (br.s, 1H), 3.40 (s, 1H), 3.97-4.16 (m, 1H), 4.25-4.34 (m, 1H), 4.53 (d, J=6.60 Hz 1H), 4.66 (d J=6.77 Hz, 1H), 5.16-5.27 (m, 2H), 5.56-5.83 (m, 1H); $^{13}$C NMR (50 MHz, CDCl$_3$): δ23.68, 44.23, 56.00, 64.51, 75.63, 94.59, 117.10, 138.06.

Example 18: (4S)-(2R,4S)-4-(methoxymethoxy)hex-5-en-2-yl 4-(methoxymethoxy)hex-5-enoate (13)

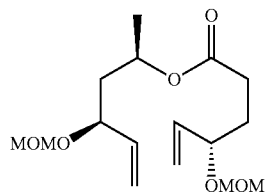

Esterification of MOM protected allylic alcohol (11) (0.5 g) with carboxylic acid compound (12) (0.6 g) was done carried by using EDCI.HCl (0.891 g) & catalytic DMAP (30 mg) in CH$_2$Cl$_2$ at 0-25° C. to obtain ester compound (13).

[α]$_D^{25}$ −125.6 (c 1.6, CH$_2$Cl$_2$); lit.$^{12}$ [α]$_D^{25}$ −127.6 (c 0.60, CHCl$_3$); IR (CHCl$_3$, cm$^{-1}$) 920, 993, 1030, 1096, 1150, 1732, 2930; $^1$H NMR (200 MHz, CDCl$_3$): δ 1.24 (d, J=6.39 Hz, 3H), 1.69-1.77 (m, 2H), 1.84-1.94 (m, 2H), 2.37-2.41 (m, 2H), 3.32 (s, 1H), 3.37 (s, 1H), 4.02 (m 2H), 4.46 (d, J=6.77 Hz, 1H), 4.51 (d, J=6.77 Hz, 1H), 4.66-4.69 (m, 2H), 5.06-5.14 (m, 1H), 5.18-5.25 (m, 4H), 5.62-5.71 (m, 2H); $^{13}$C NMR (50 MHz, CDCl$_3$): δ20.64, 30.40, 30.45, 42.09, 55.47, 55.69, 67.64, 73.66, 77.27, 93.69, 117.38, 117.81, 137.67, 137.98, 172.70.

Example 19: (6E,5S,8S,10R)-4,5,9,10-tetrahydro-5,8-bis(methoxymethoxy)-10-methyl-3H-oxecin-2(8H)-one (14)

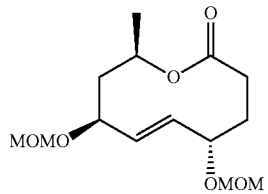

A solution of Grubbs 2nd-generation catalyst (10 mol %) in CH$_2$Cl$_2$ was added dropwise to a solution of diene (13), (2R,4S)-4-(methoxymethoxy)hex-5-en-2-yl (S)-4-(methoxymethoxy)hex-5-enoate) in CH$_2$Cl$_2$. The mixture was stirred under reflux at 45° C. for 24 h. The solvent was evaporated and the crude product purified by column chromatography.

[α]$_D^{25}$ −40.6 (c 1.6, CH$_2$Cl$_2$); lit.$^{12}$ [α]$_D^{25}$ −42.8 (c 1.21, CHCl$_3$); IR (CHCl$_3$, cm$^{-1}$) 755, 803, 1030, 1098, 1260, 1375, 1450, 1728, 1855, 1953, 2851, 1945, 2860, 2930; $^1$H NMR (200 MHz, CDCl$_3$): δ 1.23 (d, J=6.84 Hz, 3H), 1.76-1.88 (m, 2H), 1.97-2.12 (m, 3H), 2.27-2.32 (m, 1H), 3.32 (s, 1H), 3.37 (s, 1H), 4.48 (m 2H), 4.48 (d, J=6.80 Hz, 1H), 4.51 (d, J=6.77 Hz, 1H), 4.66-4.69 (m, 2H), 5.06-5.14 (m, 1H), 5.18-5.25 (m, 4H), 5.62-5.71 (m, 2H); $^{13}$C NMR (50 MHz, CDCl$_3$): δ20.64, 30.40, 30.45, 42.09, 55.47, 55.69, 67.64, 73.66, 77.27, 93.69, 117.38, 117.81, 137.67, 137.98, 172.70.

Example 20: Compound of Formula (30) ethyl (4R,7R,E)-7-((tert-butyldimethylsilyl)oxy)-4-hydroxyoct-2-enoate

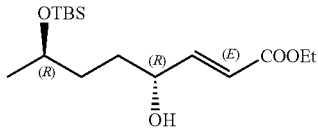

To a precooled (−20° C.) R.B. flask, solution of aldehyde (R)-5-((tert-butyldimethylsilyl)oxy)hexanal in CH$_3$CN, nitrosobenzene (1 equiv) solvent and L-proline (20 mol %) were added. The reaction mixture was stirred for 24 h at −20° C. Triethylphosphonoacetate (1.8 equiv), LiCl (1.1 equiv), DBU (1.5 equiv) were added to the above mixture at 0° C. and stirred for 2 h. On completion of reaction (by checking TLC), the solvent CH$_3$CN was evaporated, the organic layer was extracted with EtOAc and dried over anhydrous Na$_2$SO$_4$. The solvent was removed in vacuum and concentrated. To the crude Cu(OAc)$_2$ (30 mol %) was added in EtOH and stirred for 24 h. After the completion of reaction (monitored by TLC), EtOH was removed in vacuum and the crude was subjected to chromatographic separation. The eluent was allowed to come out in a solution of pet ether:EtOAc=80:20 as pale yellow oily liquid, [α]$^{25}$=+11.6 (c 1.5, CHCl3), IR (KBr): mmax 3442, 2927, 2855, 1721, 1656, 1465, 1255, 1043, 774 cm1; 1H NMR (CDCl3, 200 MHz): δ 6.89 (dd, J=15.8 Hz, 1H), 6.02 (dd, J=15.8 Hz, 1H), 4.28-4.20 (m, 1H), 4.18 (q, J=14.3, 6.8 Hz, 2H), 3.94-3.87 (m, 1H), 1.74-1.52 (m, 4H), 1.30 (t, J=6.8 Hz, 3H), 1.16 (d, J=6.8 Hz, 3H), 0.89 (s, 9H), 0.07 (s, 6H); 13C NMR (CDCl3, 50 MHz): d 166.3, 150.2, 120.0, 71.0, 68.4, 60.1, 35.3, 32.2, 25.9, 23.1, 18.1, 14.3, −4.3, −4.6.

Example 21: Compound of Formula (32) (4R,7R, E)-7-((tert-butyldimethylsilyl)oxy)-4-(methoxymethoxy)oct-2-enal

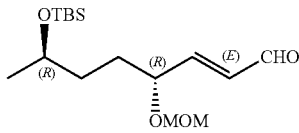

To a stirred solution of α,β-unsaturated ester (31, ethyl (4R,7R,E)-7-((tert-butyldimethylsilyl)oxy)-4-(methoxymethoxy)oct-2-enoate) dissolved in dry THF at −78° C., DIBAL-H (1 equiv) was added and stirred for 1 h. On completion of the reaction (by checking TLC), the mixture was quenched with dilute solution of potassium hydrogen tartarate (1 g, 10% aq. Sol.). The organic layer was extracted in DCM, washed with brine, dried over anhydrous Na$_2$SO$_4$. The solvent was removed in vacuum, concentrated and subjected for chromatographic separation. The eluent was allowed to come in a solution of pet ether:EtOAC=95:5 as a colorless liquid. [α]$^{25}$=+22.5 (c=1.55, CHCl3); 1H NMR (200 MHz, CDCl$_3$): 0.05 (d, 6H, J=2.0 Hz), 0.90 (s, 9H), 1.14 (d, 3H, J=6.0 Hz), 1.35-1.83 (m, 4H), 3.36 (s, 3H), 3.74-3.84 (m, 1H), 4.24-4.35 (m, 1H), 4.6 (m, 2H), 6.16-6.28 (dd, 1H, J=7.1, 7.7 Hz), 6.60-6.71 (dd, 1H, J=6.0, 5.8 Hz), 9.8 (d, 1H, J=7.7 Hz); 13C NMR (50 MHz, CDCl3): −4.8, −4.4, 23.8, 25.8, 30.8, 34.8, 55.7, 68.2, 75.5, 95.0, 132.0, 156.7, 193.3.

Example 22: Compound of Formula (33) ethyl (2Z, 4E,6R,9R)-9-((tert-butyldimethylsilyl)oxy)-6-(methoxymethoxy)deca-2,4-dienoate

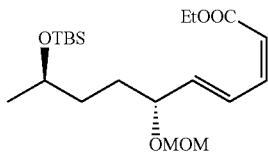

In a solution of dry THF, NaH (1.5 equiv) and Ethyl P,P-bis(2,2,2 tri fluoro ethyl) phos-phonoacetate (1.8 equiv) at −78° C. were added and stirred for 1 h. This was followed by dropwise addition of α,β-unsaturated aldehyde (32), dissolved in dry THF using a syringe to the above mixture and the reaction was stirred for another 1 h. After completion of the reaction (monitored by TLC), the mixture was quenched with ice and the organic layer was extracted using ether and washed with brine and dried over anhydrous Na$_2$SO$_4$. The solvent was removed in vacuum, concentrated and the crude was purified by chromatographic technique (EtOAc:pet ether=10:90). [α]$^{25}$=+49 (c 1.2, CHCl$_3$); 1H NMR (CDCl3, 200 MHz): 7.46 (m, 1H), 6.55 (t, 1H), 5.88 (q, 1H), 5.69 (d, 1H), 4.53-4.68 (m, 2H), 4.18 (m, 3H), 3.80 (m, 1H), 3.36 (s, 3H), 1.54-1.62 (m, 4H), 1.30 (m, 4H), 1.11 (d, 3H), 0.88 (s, 9H), 0.04 (s, 6H).

Example 23: Compound of Formula (34) ethyl (2Z, 4E,6R,9R)-9-(oxy)-6-(methoxymethoxy)deca-2,4-dienoate

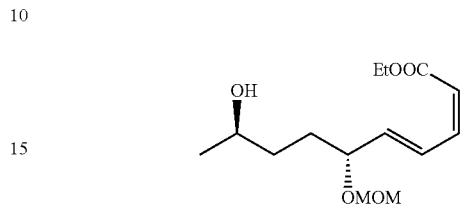

To a stirred solution of TBS protected alcohol (33, (4R, 7R,E)-7-((tert-butyldimethylsilyl)oxy)-4-(methoxymethoxy)oct-2-enal) in THF, TBAF (2 equiv) was added and stirred for 2 h. After completion of the reaction (monitored by TLC), the organic layer was extracted using ether and washed with brine and dried over dried over anhydrous Na$_2$SO$_4$. The solvent was removed in vacuum, concentrated and the crude was purified by chromatographic technique (EtOAc:pet ether=20:80). [α]25=+68 (c 0.44, CHCl3), 1H NMR (CDCl3, 200 MHz): 7.48 (m, 1H), 6.25-6.61 (m, 1H), 5.64-6.02 (m, 2H), 4.67 (m, 2H), 4.20 (m, 3H), 3.80 (m, 1H), 3.36 (s, 3H), 1.90 (br s, 1H), 1.54-1.71 (m, 4H), 1.30 (t, 3H), 1.18 (d, 3H).

Example 24: Compound of Formula (36) (3Z,5E, 7R,10R)-7-(methoxymethoxy)-10-methyl-7,8,9,10-tetrahydro-2H-oxecin-2-one

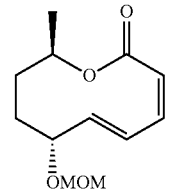

To a stirred solution of acid (35 ((2Z,4E,6R,9R)-9-(oxy)-6-(methoxymethoxy)deca-2,4-diene acid) in dry THF, 2,4, 6-trichlorobenzoylchloride (1.5 equiv), Et$_3$N (1.5 equiv) were added at 0° C. and stirred for 2 h. The reaction mixture was added to a solution of DMAP (4.5 equiv) in dry toluene at 80° C. for 24 h. On completion of reaction (by checking TLC), it was cooled to room temperature (25° C.), the solvent was evaporated, the organic layer was extracted with EtOAc and dried over anhydrous Na$_2$SO$_4$. The solvent was removed in vacuum and concentrated. The crude was purified by chromatographic technique (EtOAc:pet ether=10: 90). [α]$^{25}$=+47.4 (c=0.8, CHCl3); 1H NMR (300 MHz, CDCl3): 1.22 (d, 3H, J=6.2 Hz), 1.57-1.94 (m, 4H), 3.35 (s, 3H), 4.15 (td, 1H, J=4.0, 9.0 Hz), 4.53 (d, 1H, J=6.8 Hz), 4.70 (d, 1H, J=6.6 Hz), 5.00 (m, 1H), 5.64 (dd, 1H, J=9.6, 15.4 Hz), 5.85 (d, 1H, J=10.5 Hz), 6.16 (d, 1H, J=15.1 Hz), 6.62 (d, 1H, J=10.3 Hz); 13C NMR (75 MHz, CDCl$_3$): 21.4, 29.7, 39.0, 55.5, 73.1, 73.2, 95.0, 124.1, 128.1, 138.5, 140.6, 168.0.

Example 25: Stagonolide-E (3Z,5E,7R,10R)-7-hydroxy-10-methyl-7,8,9,10-tetrahydro-2H-oxecin-2-one

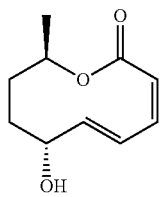

To a stirred solution of the macrolactone 36 (20 mg) in THF, 2N HCl 1 ml solution was added and stirred for 2 h at 25° C. After completion of the reaction (monitored by TLC), the organic layer was extracted using ether and washed with brine and dried over dried over anhydrous Na$_2$SO$_4$. The solvent was removed in vacuum and concentrated. The crude was purified by chromatographic technique (EtOAc: pet ether=20:80). Yield: 78%

$[\alpha]^{25}$=−180.2 (C=0.3, CHCl$_3$). 1H NMR (CDCl$_3$, 200 MHz) δ 6.62 (d, J=11.6 Hz, 1H), 6.12 (br, J=15.4 Hz, 1H), 5.85 (d, J=11.6 Hz, 1H), 5.74 (dd, J=15.3, 9.4 Hz, 1H), 4.98 (m, 1H), 4.25 (m, 1H), 1.94-1.6 (m, 4H), 1.22 (d, J=6.8 Hz, 3H); 13C NMR (CDCl3, 50 MHz): δ 168.1, 140.2, 139.4, 126.5, 125.6, 73.5, 73.2, 37.4, 30.3, 21.3.

Example 26: Compound of Formula (22) 6-(benzyloxy)hexan-1-ol

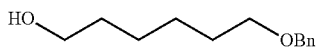

To a stirred solution of 1,6-hexan-diol in dry THF at 0° C., NaH (1.1 equiv) was added. After stirring for 30 min, BnBr (1 equiv) was added slowly dropwise using a syringe and stirred for additional 3 h. After completion of the reaction (monitored by TLC), it was quenched with ice and the organic layer was extracted using ether and washed with brine and dried over anhydrous Na$_2$SO$_4$. The solvent was removed in vacuum and concentrated. The crude was purified by chromatographic technique (EtOAc:pet ether=20:80). 1H NMR (CDCl$_3$, 200 MHz) δ 7.3-7.4 (5H, m), 4.5 (s, 2H), 3.6 (t, 2H), 3.4 (t, 2H), 1.8 (br s, 1H), 1.6 (m, 4H), 1.4 (m, 4H); 13C NMR (CDCl3, 50 MHz): 138.56, 128.34, 127.62, 127.50, 72.87, 70.29, 62.63, 32.67, 29.73, 26.03, 25.62.

Example 27: Compound of Formula (23) 6-(benzyloxy)hexanal

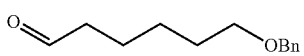 [SMILES: O=CCCCCCOCc1ccccc1]

To a solution of alcohol (22, 6-(benzyloxy)hexan-1-ol) dissolved in dry DCM, Tempo free radical (0.1 equiv), iodobenzenediacetate (1.1 equiv) were added and stirred at 25° C. On completion of the reaction (by checking TLC), it was quenched with dilute solution of Na$_2$S$_2$O$_3$. The organic layer was extracted in DCM, washed with brine, dried over anhydrous Na$_2$SO$_4$. The solvent was removed in vacuum concentrated and subjected for chromatographic separation. The eluent was allowed to come in a solution of pet ether:EtOAC=95:5 as a colorless liquid. 1H NMR (CDCl$_3$, 200 MHz): δ 9.8 (s, 1H), 7.2-7.4 (m, 5H), 4.5 (s, 2H), 3.5 (t, 2H), 2.4 (t, 2H), 1.6 (m, 4H), 1.4 (m, 4H); 13C NMR (CDCl3, 50 MHz): δ 202.75, 138.50, 128.40, 127.68, 127.50, 72.95, 70.03, 43.86, 29.53, 25.85, 21.91.

Example 28: Compound of Formula (24) (S)-6-(benzyloxy)hexane-1,2-diol

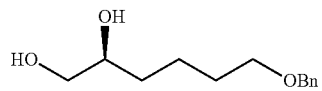 [SMILES: OC[C@@H](O)CCCCOCc1ccccc1]

To a precooled solution of aldehyde (23, 6-(benzyloxy)hexanal) in CH$_3$CN at −20° C., nitrosobenzene (1 equiv) and D-proline (20 mol %) were added, stirred for 24 h. This was followed by addition of NaBH$_4$ (2 equiv) and MeOH to the reaction mixture at 0° C. for 30 min. On completion of the reaction, solvent was evaporated and concentrated. To the crude 30 mol % CuSO4 was added in EtOH and stirred for 24 h. After the completion of reaction (monitored by TLC), EtOH was removed in vacuum and the crude was subjected to chromatographic separation. The eluent was allowed to come out in a solution of pet ether:EtOAc=60:40. 1H NMR (CDCl$_3$, 200 MHz): 7.2-7.4 (m, 5H), 4.5 (s, 2H), 3.6 (m), 2H), 3.4 (m, 3H), 2.6 (br s, 2H), 1.5 (m, 6H); 13C NMR (CDCl3, 50 MHz): 138.37, 128.39, 127.69, 127.50, 72.92, 71.64, 70.22, 66.12, 33.60, 29.64, 22.42.

Example 29: Compound of Formula (25) (S)-2-(4-(benzyloxy)butyl)oxirane

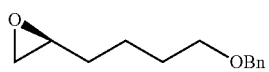 [SMILES: c1ccc(COCCCC[C@H]2CO2)cc1]

To a stirred solution of diol (24, (S)-6-(benzyloxy)hexane-1,2-diol 24) in CH$_2$Cl$_2$ solvent, TsCl (1.1 equiv), Bu$_2$SnO, DMAP (10 mol %), Et$_3$N (2 equiv) were added and stirred for 2 h. On completion of the reaction (by checking TLC), the organic layer was extracted in DCM, washed with brine, dried over anhydrous Na$_2$SO$_4$. The solvent was removed in vacuum, concentrated and subjected for chromatographic separation. The eluent was allowed to come in a solution of pet ether:EtOAC=95:5 ($[\alpha]^{25}$=5.25 (c 2.0, CHCl$_3$) 1H NMR (CDCl$_3$, 200 MHz): 7.2-7.4 (m, 5H), 4.5 (s, 2H), 3.46 (t, 2H), 2.86-2.88 (m, 1H), 2.69 (dd, J=4.0, 5.1 Hz, 1H), 2.43 (dd, J=2.8, 5.2 Hz, 1H), 1.51-1.66 (m, 6H); 13C NMR (CDCl3, 50 MHz): 138.37, 128.39, 127.69, 127.50, 72.92, 70.12, 52.1, 33.30, 29.64, 22.8.

Example 30: Compound of Formula (26) (R)-6-(benzyloxy)hexan-2-ol

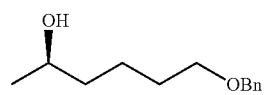

To a suspension of LiAlH$_4$ (1.1 equiv) in dry THF, a solution of epoxide (25, (S)-2-(4-(benzyloxy)butyl)oxirane) in THF was added dropwise at 0° C. The reaction mixture was stirred at this temperature for 30 min After completion of reaction (monitored by TLC), it was quenched with aq 20% solution of sodium hydroxide (2 mL) at 0° C. The reaction mixture was filtered through sintered funnel, dried over anhydrous Na$_2$SO$_4$ and concentrated. Purification by column chromatography with petroleum ether/ethyl acetate (90:10) gave the secondary alcohol as a colorless liquid. $[\alpha]^{25}$=−7.9 (c 2.0, CHCl3); IR (neat, cm$^{-1}$): 3354, 2935, 1657, 1460, 1416, 1375, 1300; 1H NMR (200 MHz, CDCl3): δ 7.29-7.33 (m, 5H), 4.48 (s, 2H), 3.70-3.79 (m, 1H), 3.46 (t, J=6.2 Hz, 2H), 2.0 (br s, 1H), 1.41-1.70 (m, 6H), 1.15 (d, J=6.2 Hz, 3H); 13C NMR (50 MHz, CDCl3): δ 138.5, 128.3, 127.6, 127.5, 72.9, 70.3, 67.6, 39.0, 29.7, 23.5, 22.4.

Example 31: Compound of Formula (27) (R)-((6-(benzyloxy)hexan-2-yl)oxy)(tert-butyl)dimethylsilane

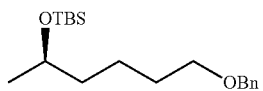 [SMILES: C[C@H](CCCCOCc1ccccc1)O[Si](C)(C)C(C)(C)C]

To a solution of alcohol (26, (R)-6-(benzyloxy)hexan-2-ol) in dry CH$_2$Cl$_2$ at 0° C. were added imidazole (1.5 equiv) and tert-butyl dimethylsilyl chloride (1.2 equiv). The reaction mixture was stirred at 25° C. for 2 h. After completion of reaction (monitored by TLC), it was diluted with CH$_2$Cl$_2$, washed with water, brine, and dried over anhydrous Na$_2$SO$_4$. Removal of the solvent under reduced pressure gave the crude product which was purified by column chromatography with pure petroleum ether to the product as a colorless liquid $[\alpha]^{25}$=−10.0 (c 1.0, CHCl3); IR (neat, cm_1): 2929, 2856, 1471, 1462, 1455, 1373, 1361; 1H NMR (200 MHz, CDCl3): δ 7.31-7.33 (m, 5H), 4.48 (s, 2H), 3.72-3.81 (m, 1H), 3.45 (t, J=6.4 Hz, 2H), 1.33-1.63 (m, 6H), 1.12 (d, J=6.1 Hz, 3H), 0.88 (s, 9H), 0.04 (s, 6H); 13C NMR (50 MHz, CDCl3): δ 138.7, 128.2, 127.5, 127.3, 72.8, 70.3, 68.4, 39.5, 29.8, 25.9, 23.8, 22.4, 18.1, −4.4, −4.7.

Example 32: Compound of Formula (28) (R)-5-((tert-butyldimethylsilyl)oxy)hexan-1-ol

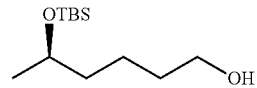

A mixture of benzyl ether, (27, (R)-((6-(benzyloxy)hexan-2-yl)oxy)(tert-butyl)dimethylsilane), 10% Pd/C, and catalytic amount of triethylamine (2 drops) was stirred under H$_2$ (1 atm) at 25° C. After completion of reaction (monitored by TLC), it was filtered through Celite (MeOH eluent) and the solvent evaporated under reduced pressure to afford the title compound as a slightly yellow colored oil. $[\alpha]^{25}$=−13:8 (c 1.6, CHCl3); IR (neat, cm_1): 3438.4, 2930.4, 2857.9, 1225.6, 1099.5, 1050.13; 1H NMR (200 MHz, CDCl3): d 3.70-3.78 (m, 1H), 3.59 (t, J=6.3 Hz, 2H), 1.62 (br s, 1H), 1.32-1.55 (m, 6H), 1.09 (d, J=6.1 Hz, 3H), 0.84 (s, 9H), 0.04 (s, 6H); 13C NMR (50 MHz, CDCl3): d 68.5, 62.6, 39.4, 32.7, 25.9, 23.7, 21.7, 18.1, −4.41, −4.71.

Example 33: Compound of Formula (29) (R)-5-((tert-butyldimethylsilyl)oxy)hexanal

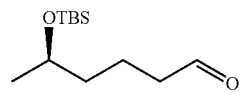

To a solution of alcohol (28, (R)-5-((tert-butyldimethylsilyl)oxy)hexan-1-ol) dissolved in dry DCM, Tempo free radical (0.1 equiv), iodobenzenediacetate (1.1 equiv) were added and stirred at 25° C. On completion of the reaction (by checking TLC), it was quenched with dilute solution of Na$_2$S$_2$O$_3$. The organic layer was extracted in DCM, washed with brine, dried over anhydrous Na$_2$SO$_4$. The solvent was removed in vacuum, concentrated and subjected for chromatographic separation. The eluent was allowed to come in a solution of pet ether:EtOAC=95:5 as a colorless liquid. $[\alpha]^{25}$=−12:0 (c 3.0, CHCl3); IR (neat, cm-1): 3020, 2930, 2857, 1722, 1572, 1472, 1215; 1H NMR (200 MHz, CDCl3): δ 9.71 (t, J=1.8 Hz, 1H), 3.71-3.83 (m, 1H), 2.33-2.39 (dt, J=7.1, 8.8 Hz, 2H), 1.54-1.70 (m, 2H), 1.35-1.43 (m, 2H), 1.09 (d, J=6.0 Hz, 3H), 0.84 (s, 9H), 0.05 (s, 6H); 13C NMR (50 MHz, CDCl3): δ 202.0, 67.6, 43.4, 38.46, 25.40, 23.26, 17.85, 17.59, −4.84, −5.23.

Example 34: Compound of Formula (31) ethyl (4R, 7R,E)-7-((tert-butyldimethylsilyl)oxy)-4-(methoxymethoxy)oct-2-enoate

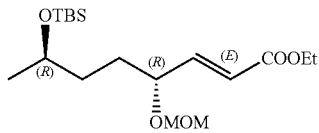

To a stirred solution of the compound (30, ethyl (4R,7R, E)-7-((tert-butyldimethylsilyl)oxy)-4-hydroxyoct-2-enoate) in dry CH$_2$Cl$_2$ solvent, MOMCl (2 equiv), DIPEA (3 equiv) were added and stirred for 8 h. On completion of the reaction (by checking TLC), the organic layer was extracted in DCM, washed with brine, dried over anhydrous Na$_2$SO$_4$. The solvent was removed in vacuum, concentrated and subjected for chromatographic separation. The eluent was allowed to come in a solution of pet ether:EtOAC=90:10 as a pale yellow liquid $[\alpha]^{25}$=+23.22 (c 1.24, CHCl$_3$); 1H NMR (200 MHz, CDCl3): δ 6.69-6.80 (dd, 1H), 5.96 (d, 1H), 4.57 (m, 2H), 4.14 (m, 3H), 3.81 (m, 1H), 1.40 (t, 3H), 1.23 (d, 2H), 0.84 (s, 9H), −0.4 (s, 6H); 13C NMR (CDCl3, 50 MHz): 166.04, 147.76, 121.95, 94.48, 75.04, 68.07, 60.37, 55.55, 34.94, 30.78, 25.92, 23.85, 18.12, 14.28, −4.29, −4.67.

Example 35: Stagonolide C

Me$_3$SiBr (0.8 ml, 0.45 mmol) was added dropwise to a cold (−40° C.) stirred solution of 21 (43 mg, 0.15 mmol) in CH$_2$Cl$_2$ (50 ml). The reaction mixture was stirred at −40° C. for 2 h. After the completion of reaction (monitored by TLC), the reaction mixture was poured into saturated aq. NaHCO$_3$ solution, and extracted with CH$_2$Cl$_2$. The organic layer was dried over anhydrous Na$_2$SO$_4$, and concentrated under reduced pressure to give the crude product. The residue was then purified with column chromatography using petroleum ether: EtOAc (6:4 v/v) to give stagonolide C (20 mg) as a colorless liquid.

Yield: 76%; [α]$_D^{25}$+44.7 (c 0.9, CHCl$_3$); {lit.$^{4d}$[α]$_D^{25}$+ 45.6 (c 1.0, CHCl$_3$)}; IR (CHCl$_3$): υ$_{max}$ 3385, 2926, 2850, 1720, 1445, 1370, 1098, 1235, 1110, 1040 cm$^{-1}$; $^1$H NMR (200 MHz, CDCl$_3$): δ 1.24 (d, J=6.8 Hz, 3H), 1.72-1.96 (m, 2H), 1.99-2.10 (m, 3H), 2.20-2.34 (m, 1H), 4.02-4.14 (m, 2H), 5.06-5.20 (m, 1H), 5.41 (dd, J=8.9, 15.8 Hz, 1H), 5.56 (dd, J=9.0, 16.1 Hz, 1H); $^{13}$C NMR (50 MHz, CDCl$_3$): δ 22.0, 31.5, 34.4, 43.3, 67.4, 72.1, 74.5, 132.9, 174.0; Anal. Calcd for C$_{10}$H$_{16}$O$_4$ requires C, 59.98; H, 8.05. found C, 60.03; H, 8.12%.

Example 36: Aspinolide A

To a well stirred solution of silyl ether 28 (200 mg, 0.48 mmol) in dry THF (5 mL) was added 1 M solution of tetrabutylammonium fluoride (1 mL, 1 mmol) at 0° C. The reaction mixture was stirred at this temperature for additional 2 h. After the completion of reaction (monitored by TLC), it was quenched with H$_2$O (1 mL) and the reaction mixture extracted with Et$_2$O (3×20 mL). then washed with brine, dried over anhydrous Na$_2$SO$_4$. After the removal of solvent, the crude product was dissolved in freshly distilled degassed anhydrous CH$_2$Cl$_2$ (50 mL). The reaction mixture was treated with Grubb's II catalyst (82 mg, 20 mol %) and heated at reflux for 24 h under inert atmosphere. After the completion of reaction (monitored by TLC), the solvent was then distilled off and the residue was purified by column chromatography with petroleum ether/EtOAc (9:1 v/v) to afford 2 (54 mg) as a viscous liquid.

Yield: 69%; [α]$_D^{25}$ −40.7 (c 0.3, MeOH) {lit.$^{4e}$ [α]$_D^{25}$ −41.6 (c 0.25, MeOH)}; IR (CHCl$_3$): υ$_{max}$ 3436, 2920, 2852, 1730, 970, 1460, 1275 cm$^{-1}$; $^1$H NMR (200 MHz, CDCl$_3$): δ 1.29 (d, J=6.1 Hz, 3H), 1.52-1.89 (m, 4H), 2.30 (t, J=7.1 Hz, 2H), 2.40-2.42 (m, 2H), 3.97-4.06 (m, 1H), 5.02-5.07 (m, 1H), 5.23 (d, J=7.6 Hz, 1H), 5.59-5.72 (m, 1H); $^{13}$C NMR (50 MHz, CDCl$_3$): δ 19.7, 22.3, 35.5, 38.6, 42.1, 71.8, 74.6, 131.7, 137.4, 176.5; Analysis: C$_{10}$H$_{16}$O$_3$ requires C, 65.19; H, 8.75. found C, 65.11; H, 8.86.

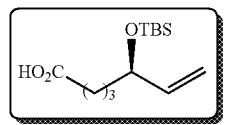

Example 37: Compound 15

(R)-3-(tert-butyldimethylsilyloxy)pent-4-enoic acid, 14

To a solution of alcohol (15.0 g) in CH$_3$CN/H$_2$O (4:1) was added in one portion bis-acetoxy iodobenzene (24.34, 75.6 mmol) and TEMPO (1.07 g, 6.9 mmol). The reaction mixture was then allowed to stir at 25° C. for 4 h. After completion of reaction (monitored by TLC), the reaction mixture was quenched by addition of saturated solution of aq. ammoniumthiosulphate. The organic layer was separated, washed with brine and subjected to column chromatographic purification with petroleum ether/EtOAc (9:1 v/v) to afford the acid 15.

Yield: 80%; [α]$_D^{25}$ −6.5 (c 1.0, CHCl$_3$); IR (CHCl$_3$): 3444, 3070, 2931, 2858, 1707, 1462, 1425, 1257, 1109 cm$^{-1}$; $^1$H NMR (200 MHz, CDCl$_3$): δ 0.03 (s, 3H), 0.05 (s, 3H), 0.89 (s, 9H), 1.47-1.76 (m, 4H), 2.32-2.39 (t, J=6.10 Hz, 2H), 4.07-4.15 (m, 1H), 5.01-5.19 (m, 2H), 5.69-5.86 (m, 1H); $^{13}$C NMR (50 MHz, CDCl$_3$): δ −4.92, −4.43, 18.17, 20.22, 25.82, 29.64, 33.96, 37.08, 73.28, 113.94, 141.19, 179.90; Anal. Calcd for C$_{11}$H$_{22}$O$_3$Si requires C, 57.35; H, 9.63. found C, 57.45; H, 9.68%.

Advantages of Invention

Thus the present invention provides cost effective, non-toxic improved process for asymmetric synthesis of highly enantioselective decanolides in good yield from cheaper, non-chiral, easily available starting material.

The naturally available proline based catalyst is used for introduction of chirality that enhances the enantioselectivity of the desired decanolides and makes the process environmental friendly. Further by avoiding expensive and toxic metal catalyst present inventors have improved upon the economics of the process. Also, the present process improves the overall yield by reducing lengthy process steps.

We claim:

1. An organo catalytic process for the preparation of decanolides of Formula Ic

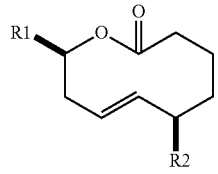

Formula Ic wherein the said process comprising the steps of:

i) allylboration of aldehyde (1)

(1)

in presence of allyldiisopinocamphenylborane at temperature in the range of −120° C. to −80° C. for 1-2 hours in non-polar organic solvents selected from the group consisting of diethyl ether, pentane, cyclopentane, benzene, toluene, 1,4-dioxane, chloroform, and mixtures thereof followed by treatment with NaOH and aqueous H$_2$O$_2$ to obtain chiral allylic alcohol (3)

(3)

ii) esterification of allylic alcohol (3) with butyldimethylsilyl(TBS) protected carboxylic acid (15)

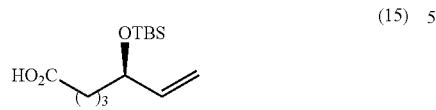
(15)

in presence of N-(3-dimethylaminopropyl)-N'-ethyl-carbodiimide hydrochloride, 4-dimethylaminopyridine in DCM at temperature range 0° to 30° C. for 5 to 8 hours with subsequent deprotection of TBS in presence of tetra-n-butylammonium fluoride in THF for 6-8 hours yields allylic alcohol (17)

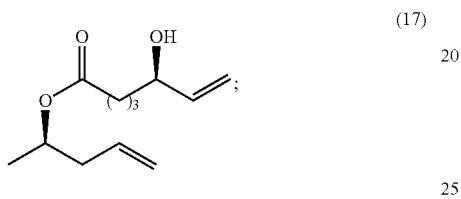
(17)

and iii) ring closing metathesis reaction of compound (17) in presence of Grubbs II catalyst (5 to 15%) in dry $CH_2Cl_2$ for 18-24 hours to obtain decanolides of Formula Ic.

* * * * *